United States Patent
D'Andrea et al.

(10) Patent No.: US 10,653,676 B2
(45) Date of Patent: *May 19, 2020

(54) SMALL MOLECULE INHIBITORS OF USP1 DEUBIQUITINATING ENZYME ACTIVITY

(71) Applicants: Dana-Farber Cancer Institute, Inc., Boston, MA (US); The Brigham and Women's Hospital, Inc., Boston, MA (US)

(72) Inventors: Alan D. D'Andrea, Winchester, MA (US); Gregory D. Cuny, Houston, TX (US); Ross L. Stein, Cambridge, MA (US); Marcie Glicksman, Winchester, MA (US); April Case, Watertown, MA (US); Jun Xian, Sharon, MA (US); David Wilson, Lawrence, KS (US); Min Huang, Shanghai (CN)

(73) Assignees: Dana-Farber Cancer Institute, Inc., Boston, MA (US); The Brigham and Women's Hospital, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/342,175

(22) Filed: Nov. 3, 2016

(65) Prior Publication Data

US 2017/0202810 A1    Jul. 20, 2017

Related U.S. Application Data

(62) Division of application No. 13/695,036, filed as application No. PCT/US2011/034514 on Apr. 29, 2011, now Pat. No. 9,518,032.

(60) Provisional application No. 61/329,984, filed on Apr. 30, 2010.

(51) Int. Cl.

| | |
|---|---|
| A61K 31/423 | (2006.01) |
| C07D 405/06 | (2006.01) |
| C07D 263/60 | (2006.01) |
| A61K 31/136 | (2006.01) |
| A61K 31/472 | (2006.01) |
| A61K 31/4725 | (2006.01) |
| A61K 45/06 | (2006.01) |
| C07C 225/30 | (2006.01) |
| C07D 217/24 | (2006.01) |

(52) U.S. Cl.
CPC ......... *A61K 31/423* (2013.01); *A61K 31/136* (2013.01); *A61K 31/472* (2013.01); *A61K 31/4725* (2013.01); *A61K 45/06* (2013.01); *C07C 225/30* (2013.01); *C07D 217/24* (2013.01); *C07D 263/60* (2013.01); *C07D 405/06* (2013.01)

(58) Field of Classification Search
CPC .................................................. A61K 31/423
See application file for complete search history.

(56) References Cited

U.S. PATENT DOCUMENTS

| | | | |
|---|---|---|---|
| 3,039,925 A | 6/1962 | Gerhard et al. | |
| 5,217,964 A | 6/1993 | Edwards et al. | |
| 5,354,782 A | 10/1994 | Edwards et al. | |
| 5,434,145 A | 7/1995 | Edwards et al. | |
| 5,645,988 A * | 7/1997 | Vande Woude ...... | A61K 31/335 435/32 |
| 5,789,431 A | 8/1998 | Lee et al. | |
| 6,114,394 A | 9/2000 | Edwards et al. | |
| 6,174,918 B1 | 1/2001 | Lee et al. | |
| 6,262,095 B1 | 7/2001 | Boutherin-Falson et al. | |
| 6,287,858 B1 | 9/2001 | D'Andrea et al. | |
| 7,041,994 B2 | 5/2006 | Hayashi et al. | |
| 7,459,287 B2 | 12/2008 | D'Andrea | |
| 7,754,463 B2 | 7/2010 | D'Andrea | |
| 7,858,331 B2 | 12/2010 | D'Andrea et al. | |
| 8,518,660 B2 | 8/2013 | Chelur et al. | |
| 8,541,192 B2 | 9/2013 | D'Andrea | |
| 9,518,032 B2 | 12/2016 | D'Andrea et al. | |
| 9,725,425 B1 | 8/2017 | D'Andrea et al. | |
| 2004/0053324 A1 | 3/2004 | Wong et al. | |
| 2008/0167229 A1 | 7/2008 | D'Andrea | |
| 2009/0062196 A1 * | 3/2009 | D'Andrea ............ | C12Q 1/6886 514/19.5 |
| 2009/0081237 A1 | 3/2009 | D'Andrea et al. | |
| 2010/0330599 A1 | 12/2010 | D'Andrea | |
| 2013/0253005 A1 | 9/2013 | D'Andrea et al. | |

FOREIGN PATENT DOCUMENTS

| | | |
|---|---|---|
| DE | 1111190 B | 7/1961 |
| DE | 2156317 A1 | 5/1973 |
| EP | 2 580 344 B1 | 11/2014 |

(Continued)

OTHER PUBLICATIONS

Invitation to Pay Additional Fees for PCT/US2011/034514 mailed Aug. 15, 2011.

(Continued)

*Primary Examiner* — Sarah Pihonak
*Assistant Examiner* — Jason Deck
(74) *Attorney, Agent, or Firm* — Wolf, Greenfield & Sacks, P.C.

(57) ABSTRACT

Provided are small molecule inhibitors of ubiquitin specific protease 1 (USP1) activity and methods for their use in treating and characterizing cancers. The small molecule USP1 inhibitors of the invention are particularly useful in the treatment of cancers that are resistant to DNA cross-linking agents.

12 Claims, 11 Drawing Sheets

Specification includes a Sequence Listing.

(56) References Cited

FOREIGN PATENT DOCUMENTS

| | | | |
|---|---|---|---|
| GB | 2 146 653 A | 4/1985 | |
| JP | 2011-042606 A | 3/2011 | |
| WO | WO 92/19211 A2 | 11/1992 | |
| WO | WO 95/11680 A1 | 5/1995 | |
| WO | WO 97/21684 A1 | 6/1997 | |
| WO | WO 97/21710 A1 | 6/1997 | |
| WO | WO 97/30022 A1 | 8/1997 | |
| WO | WO-9730022 A1 * | 8/1997 | ........... C07C 233/32 |
| WO | WO 98/37076 A1 | 8/1998 | |
| WO | WO 2005/053609 A2 | 6/2005 | |
| WO | WO-2005053609 A2 * | 6/2005 | ............ A61K 31/12 |
| WO | WO 2007/120574 A2 | 10/2007 | |
| WO | WO 2007/149484 A2 | 12/2007 | |
| WO | WO 2008/030369 A1 | 3/2008 | |
| WO | WO 2011/113060 A2 | 9/2011 | |
| WO | WO 2011/137320 A2 | 11/2011 | |

OTHER PUBLICATIONS

International Search Report and Written Opinion for PCT/US2011/034514 dated Nov. 4, 2011.
International Preliminary Report on Patentability for PCT/US2011/034514 dated Nov. 15, 2012.
International Search Report and Written Opinion for PCT/US2007/014378 dated May 27, 2008.
International Preliminary Report on Patentability for PCT/US2007/014378 dated Jan. 8, 2009.
[No Author Listed], beta-Lapachone, ARQ-501, CO-501, 4707-32-8, C15-H14-O3,2,2-Dim. Oct. 25, 2004; http://www.chemdrug.com/databases/8_0_vgbapjppdvcqsfww.html [last accessed Jan. 15, 2013]. 7 pages.
[No Author Listed], Cisplatin. Wikipedia. http://en.wikipedia.org/wiki/Cisplatin [last accessed Mar. 2, 2010]. 5 pages.
[No Author Listed], Definition of imides. Chemistry Dictionary. 1 page. http://www.chemicool.com/definition/imides.html [last accessed Mar. 31, 2010].
Aleksandrov et al., Oxidation products of fused 2-hetarylimidazole derivatives. Russian Journal of General Chemistry. Aug. 2011;81(8):1716-19.
Aly et al., Facile synthesis of new imidazole from direct reaction of 2,3-diamino-1,4-naphthoquinone with aldehydes. J Heterocyclic Chem. 2011;48(4):787-91.
Avvakumov et al.,Amino-terminal dimerization, NRDP1-rhodanese interaction, and inhibited catalytic domain conformation of the ubiquitin-specific protease 8 (USP8). J Biol Chem. Dec. 8, 2006;281(49):38061-70. Epub Oct. 11, 2006.
Babu et al., Synthesis of some substituted naphtho[2,3-d]thiazole-4,9-diones as potential fungicides. Current Science. 1967;36(7):176.
Benedetti-Doctorovich et al., Synthesis of 2-methyl-(Z)-4-(phenylimino)naphth[2,3-d]oxazol-9-one, a monoimine quinone with selective cytotoxicity toward cancer cells. J Med Chem. Mar. 4, 1994;37(5):710-2.
Berghot, New unexpected products during heteroannulation of 1,4-naphthoquinone derivatives. Chemical Papers. 2002;56(3):202-7.
Berlin et al., Regulation of epidermal growth factor receptor ubiquitination and trafficking by the USP8•STAM complex. J Biol Chem. Nov. 5, 2010;285(45):34909-21. doi:10.1074/jbc.M109.016287. Epub Aug. 24, 2010.
Boothman et al., Inhibition of radiation-induced neoplastic transformation by beta-lapachone. Proc Natl Acad Sci U S A. Jul. 1989;86(13):4963-7.
Brandy et al., Synthesis and cytotoxic activities of some 2-Arylnaphtho[2,3-d]oxazole-4,9-dione derivatives on androgen-dependent (LNCaP) and androgen-independent (PC3) human prostate cancer cell lines. Investigational New Drugs. 2012;30(4):1709-14.
Brandy et al., Synthesis and cytotoxic activities of some 2-Arylnaphtho[2,3-d]oxazole-4,9-dione derivatives on androgen-dependent (LNCaP) and androgen-independent (PC3) human prostate cancer cell lines. Investigational New Drugs—Short Report. Online. Abstract Only. Jan. 18, 2011. 2 pages. http://www.springerlink.com/content/t8213654w5332083/ [last accessed Oct. 8, 2011].
Bryant et al., Specific killing of BRCA2-deficient tumours with inhibitors of poly(ADP-ribose) polymerase. Nature. Apr. 14, 2005;434(7035):913-7. Erratum in: Nature. May 17, 2007;447(7142):346.
Burska et al., Deubiquitinating enzyme Usp12 is a novel co-activator of the androgen receptor. J Biol Chem. Nov. 8, 2013;288(45):32641-50. doi:10.1074/jbc.M113.485912. Epub Sep. 21, 2013.
Byun et al., USP8 is a novel target for overcoming gefitinib resistance in lung cancer. Clin Cancer Res. Jul. 15, 2013;19(14):3894-904. doi: 10.1158/1078-0432.CCR-12-3696. Epub Jun. 7, 2013.
Chen et al., Sequence and expression in *Escherichia coli* of the 40-kDa subunit of activator 1 (replication factor C) of HeLa cells. Proc Natl Acad Sci U S A. Apr. 1, 1992;89(7):2516-20.
Chirnomas et al., Chemosensitization to cisplatin by inhibitors of the Fanconi anemia/BRCA pathway. Mol Cancer Ther. Apr. 2006;5(4):952-61.
Clark, The fungicidal activity of substituted 1,4-naphthoquinones. Part III: amino, anilino and acylamino derivatives. Pesticide Science. 1985;16(1):23-32.
Cohen et al., CD4+ T-cells from mice immunized to syngeneic sarcomas recognize distinct, non-shared tumor antigens. Cancer Res. Feb. 15, 1994;54(4):1055-8.
Cohn et al., A UAF1-containing multisubunit protein complex regulates the Fanconi anemia pathway. Mol Cell. Dec. 14, 2007;28(5):786-97.
Cohn et al., UAF1 is a subunit of multiple deubiquitinating enzyme complexes. J Biol Chem. Feb. 20, 2009;284(8):5343-51. Epub Dec. 15, 2008.
Colland et al., Small-molecule inhibitor of USP7/HAUSP ubiquitin protease stabilizes and activates p53 in cells. Mol Cancer Ther. Aug. 2009;8(8):2286-95. Epub Aug. 11, 2009.
Colland, The therapeutic potential of deubiquitinating enzyme inhibitors. Biochem Soc Trans. Feb. 2010;38(Pt 1):137-43.
D'Andrea et al., The Fanconi Anemia and Breast Cancer Susceptibility Pathways. N Engl J Med. May 20, 2010;362(20):1909-19.
Dang et al., Kinetic and mechanistic studies on the hydrolysis of ubiquitin C-terminal 7-amido-4-methylcoumarin by deubiquitinating enzymes. Biochemistry. Feb. 17, 1998;37(7):1868-79.
De Oliveira et al., Synthesis and antimicrobial evaluation of oxazole-1,4-naphthquinones. Heterocyclic communications. 2002;8(2):199-204.
Efimova et al., Heterocyclic derivatives of substituted 1,4-naphthoquinones. IV Condensation of 2,3-diamino-1,4-naphthoquinone and its monomethyl derivative with 1,3-diketones. Zhurnal Organicheskoi Khimii. 1967;3(1):162-8.
Eiden et al., 4-Pyrones. 39. 2-Amino-4-hydroxychromones. Archiv der Pharmazie. 1972;305(9):698-701.
Farmer et al., Targeting the DNA repair defect in BRCA mutant cells as a therapeutic strategy. Nature. Apr. 14, 2005;434(7035):917-21.
Fields et al., A novel genetic system to detect protein-protein interactions. Nature. Jul. 20, 1989;340(6230):245-6.
Fong et al., Inhibition of poly(ADP-ribose) polymerase in tumors from BRCA mutation carriers. N Engl J Med. Jul. 9, 2009;361(2):123-34. Epub Jun. 24, 2009.
Fong et al., Poly(ADP)-ribose polymerase inhibition: frequent durable responses in BRCA carrier ovarian cancer correlating with platinum-free interval. J Clin Oncol. May 20, 2010;28(15):2512-9. Epub Apr. 20, 2010.
Fujiwara et al., Identification and chromosomal assignment of USP1, a novel gene encoding a human ubiquitin-specific protease. Genomics. Nov. 15, 1998;54(1):155-8.
Gao et al., Study on preparation of polyheterocyclic quinoid compounds and their third-order nonlinear optical properties. Gaojishu Tongxun. 1999;9(2):45-9.
Gao et al., Third-order nonlinear optical properties of polyheterocyclic quinoid compounds. Gongneng Cailiao. 1998;29(3):314-6.

(56) References Cited

OTHER PUBLICATIONS

Gavin et al., Functional organization of the yeast proteome by systematic analysis of protein complexes. Nature. Jan. 10, 2002;415(6868):141-7.
Gavin et al., Proteome survey reveals modularity of the yeast cell machinery. Nature. Mar. 30, 2006;440(7084):631-6. Epub Jan. 22, 2006.
Gayle et al., Identification of regions in interleukin-1 alpha important for activity. J Biol Chem. Oct. 15, 1993;268(29):22105-11.
Genbank Submission; NIH/NCBI, Accession No. AAH26072. Strausberg et al., Jul. 17, 2006. 2 pages.
Genbank Submission; NIH/NCBI, Accession No. EAW81771. Venter et al., Dec. 18, 2006. 2 pages.
Genbank Submission; NIH/NCBI, Accession No. NM_182649; Masuo et al.; Nov. 1, 2009. 4 pages.
Genbank Submission; NIH/NCBI, Accession No. NP_065890. Cohn et al., Mar. 12, 2010. 2 pages.
Genbank Submission; NIH/NCBI, Accession No. NP_073743. Cohn et al., Mar. 5, 2010. 2 pages.
Hamaguchi et al., RK-682, a potent inhibitor of tyrosine phosphatase, arrested the mammalian cell cycle progression at G1phase. FEBS Lett. Sep. 18, 1995;372(1):54-8.
Hammam et al., Heterocyclic quinones. XVI. The reaction of acid amides with 2,3-dichloro-1,4-naphthoquinone, a novel route to naphth[2,3-d]oxazole-4,9-diones. Journal fuer Praktische Chemie. 1977;319(2):254-8.
Hay et al., Poly(ADP-ribose) polymerase-1 inhibitor treatment regresses autochthonous Brca2/p53-mutant mammary tumors in vivo and delays tumor relapse in combination with carboplatin. Cancer Res. May 1, 2009;69(9):3850-5. Epub Apr. 21, 2009.
Hershko et al., Ubiquitin-aldehyde: a general inhibitor of ubiquitin-recycling processes. Proc Natl Acad Sci USA. Apr. 1987;84(7):1829-33.
Hirsch et al., Epidermal growth factor receptor in non-small-cell lung carcinomas: correlation between gene copy number and protein expression and impact on prognosis. J Clin Oncol. Oct. 15, 2003;21(20):3798-807. Epub Sep. 2, 2003.
Hirsch et al., Increased EGFR gene copy number detected by fluorescent in situ hybridization predicts outcome in non-small-cell lung cancer patients treated with cetuximab and chemotherapy. J Clin Oncol. Jul. 10, 2008;26(20):3351-7. doi: 10.1200/JCO.2007. 14.0111.
Ho et al., Systematic identification of protein complexes in *Saccharomyces cerevisiae* by mass spectrometry. Nature. Jan. 10, 2002;415(6868):180-3.
Hoege et al., RAD6-dependent DNA repair is linked to modification of PCNA by ubiquitin and SUMO. Nature. Sep. 12, 2002;419(6903):135-41.
Hu et al., Crystal structure of a UBP-family deubiquitinating enzyme in isolation and in complex with ubiquitin aldehyde. Cell. Dec. 27, 2002;111(7):1041-54.
Huang et al., HAUSP hunting the FOX(O). Nat Cell Biol. Oct. 2006;8(10):1043-5.
Huang et al., Regulation of DNA repair by ubiquitylation. Nat Rev Mol Cell Biol. May 2006;7(5):323-34.
Huang et al., Regulation of monoubiquitinated PCNA by DUB autocleavage. Nat Cell Biol. Apr. 2006;8(4):339-47. Epub Mar. 12, 2006.
Ingvarsdottir et al., H2B ubiquitin protease Ubp8 and Sgf11 constitute a discrete functional module within the *Saccharomyces cerevisiae* SAGA complex. Mol Cell Biol. Feb. 2005;25(3):1162-72.
Katz et al., Effect of the structure of exogenous quinone on its ability to function as the primary quinone in the reaction centers from Rhodobacter sphaeroides R-26. Biologicheskie Membrany. 1991;8(5):468-75.
Kee et al., Expanded roles of the Fanconi anemia pathway in preserving genomic stability. Genes Dev. Aug. 15, 2010;24(16):1680-94.
Kee et al., WDR20 regulates activity of the USP12 x UAF1 deubiquitinating enzyme complex. J Biol Chem. Apr. 9, 2010;285(15):11252-7. Epub Feb. 10, 2010.
Kennedy et al., The Fanconi Anemia/BRCA pathway: new faces in the crowd. Genes Dev. Dec. 15, 2005;19(24):2925-40.
Kim et al., Inactivation of murine Usp1 results in genomic instability and a Fanconi anemia phenotype. Dev Cell. Feb. 2009;16(2):314-20.
Kita et al., An Intramolecular Cyclization of Phenol Derivatives Bearing Aminoquinones Using a Hypervalent Iodine Reagent. 1996;61(1):223-7.
Kohli et al., Biomarker-based targeting of the androgen-androgen receptor axis in advanced prostate cancer. Adv Urol. 2012;2012:781459. doi: 10.1155/2012/781459. Epub Aug. 22, 2012.
Korkhova et al., Derivatives of 2-benzazepine from 3-substituted 2-methylamino-1,4-naphthoquinones. Zhurnal Organicheskoi Khimii. 1975;11(10):2140-4.
Krieg et al., Synthesis of 1,4-diazepines. Liebigs Annalen der Chemie. 1988;8:799-801.
Krogan et al., Global landscape of protein complexes in the yeast *Saccharomyces cerevisiae*. Nature. Mar. 30, 2006;440(7084):637-43. Epub Mar. 22, 2006.
Kuznetsov et al., Heterocyclic derivatives based on substituted 1,4-naphthoquinones. I. Naphth[2,3-d]imidazole-4,9-diones. Zhurnal Organicheskoi Khimii. 1965;1(8):1458-65.
Kuznetsov et al., Polarographic study of ring-substituted naphtho[2,3-d]imidazole-4,9-diones and their quaternary salts. Zhurnal Obshchei Khimii. 1967;37(8):1802-9.
Le Texier et al., A biosynthetic microbial ability applied for the oxidative ring cleavage of non-natural heterocyclic quinones. Tetrahedron Letters. 2001;42(25):4135-7.
Lee et al., The deubiquitylation activity of Ubp8 is dependent upon Sgf11 and its association with the SAGA complex. Mol Cell Biol. Feb. 2005;25(3):1173-82.
Lien et al., Synthesis and antiplatelet, antiinflammatory, and antiallergic activities of 2-substituted 3-chloro-1,4-naphthoquinone derivatives. Bioorg Med Chem. Dec. 1997;5(12):2111-20. Erratum in: Bioorg Med Chem Feb. 1998;6(2):251.
Liu et al., Discovery of inhibitors that elucidate the role of UCH-L1 activity in the H1299 lung cancer cell line. Chem Biol. Sep. 2003;10(9):837-46.
Luchansky et al., Substrate recognition and catalysis by UCH-L1. Biochemistry. Dec. 12, 2006;45(49):14717-25.
Lynch et al., Activating mutations in the epidermal growth factor receptor underlying responsiveness of non-small-cell lung cancer to gefitinib. N Engl J Med. May 20, 2004;350(21):2129-39. Epub Apr. 29, 2004.
Mermerian et al., Structure-activity relationship, kinetic mechanism, and selectivity for a new class of ubiquitin C-terminal hydrolase-L1 (UCH-L1) inhibitors. Bioorg Med Chem Lett. Jul. 1, 2007;17(13):3729-32. Epub Apr. 10, 2007.
Mikhnovs'Ka et al., Antimicrobial properties of some imidazole derivatives. Mikrobiologichnii Zhurnal. 1967;29(3):242-6.
Mistry et al., Small-molecule inhibitors of USP1 target ID1 degradation in leukemic cells. Mol Cancer Ther. Dec. 2013;12(12):2651-62. doi:10.1158/1535-7163.MCT-13-0103-T. Epub Oct. 15, 2013.
Mizuno et al., Regulation of epidermal growth factor receptor down-regulation by UBPY-mediated deubiquitination at endosomes. Mol Biol Cell. Nov. 2005;16(11):5163-74. Epub Aug. 24, 2005.
Moldovan et al., How the fanconi anemia pathway guards the genome. Annu Rev Genet. 2009;43:223-49.
Mulloy et al., Epidermal growth factor receptor mutants from human lung cancers exhibit enhanced catalytic activity and increased sensitivity to gefitinib. Cancer Res. Mar. 1, 2007;67(5):2325-30.
Nakanishi et al., Human Fanconi anemia monoubiquitination pathway promotes homologous DNA repair. Proc Natl Acad Sci U S A. Jan. 25, 2005;102(4):1110-5. Epub Jan. 13, 2005.
Nakatani et al., Immunoaffinity purification of mammalian protein complexes. Methods Enzymol. 2003;370:430-44.
Nicholson et al., EGFR and cancer prognosis. Eur J Cancer. Sep. 2001;37 Suppl 4:S9-15.

(56) References Cited

OTHER PUBLICATIONS

Niendorf et al., Essential role of ubiquitin-specific protease 8 for receptor tyrosine kinase stability and endocytic trafficking in vivo. Mol Cell Biol. Jul. 2007;27(13):5029-39. Epub Apr. 23, 2007.

Nijman et al., A genomic and functional inventory of deubiquitinating enzymes. Cell. Dec. 2, 2005;123(5):773-86.

Nijman et al., The deubiquitinating enzyme USP1 regulates the Fanconi anemia pathway. Mol Cell. Feb. 4, 2005;17(3):331-9.

Oestergaard et al., Deubiquitination of FANCD2 is required for DNA crosslink repair. Mol Cell. Dec. 14, 2007;28(5):798-809.

Park et al., Herpesviral protein targets a cellular WD repeat endosomal protein to downregulate T lymphocyte receptor expression. Immunity. Aug. 2002;17(2):221-33.

Pickart et al., Ubiquitin: structures, functions, mechanisms. Biochim Biophys Acta. Nov. 29, 2004;1695(1-3):55-72.

Prescott, Potential antimalarial agents. Derivatives of 2-chloro-1,4-naphthoquinone. J Med Chem. Jan. 1969;12(1):181-2.

Priolo et al., The isopeptidase USP2a protects human prostate cancer from apoptosis. Cancer Res. Sep. 1, 2006;66(17):8625-32.

Qui et al., hRpn13/ADRM1/GP110 is a novel proteasome subunit that binds the deubiquitinating enzyme, UCH37. EMBO J. Dec. 13, 2006;25(24):5742-53. Epub Nov. 30, 2006.

Renatus et al., Structural basis of ubiquitin recognition by the deubiquitinating protease USP2. Structure. Aug. 2006;14(8):1293-302.

Rumpf et al., Functional division of substrate processing cofactors of the ubiquitin-selective Cdc48 chaperone. Mol Cell. Jan. 20, 2006;21(2):261-9.

Shan et al., Suppression of cancer cell growth by promoting cyclin D1 degradation. Mol Cell. Nov. 13, 2009;36(3):469-76. doi:10.1016/j.molcel.2009.10.018.

Sharma et al., Epidermal growth factor receptor mutations in lung cancer. Nat Rev Cancer. Mar. 2007;7(3):169-81.

Simonetti et al., Detection of EGFR mutations with mutation-specific antibodies in stage IV non-small-cell lung cancer. J Transl Med. Dec. 18, 2010;8:135. doi:10.1186/1479-5876-8-135.

Sondhi et al., A Convenient, Solvent Free and High Yielding Synthesis of Bicyclo-Heterocyclic Compounds. Lett. Org. Chem. Jan. 2008;5(1):51-54.

Sordella et al., Gefitinib-sensitizing EGFR mutations in lung cancer activate anti-apoptotic pathways. Science. Aug. 20, 2004;305(5687):1163-7. Epub Jul. 29, 2004.

Sowa et al., Defining the human deubiquitinating enzyme interaction landscape. Cell. Jul. 23, 2009;138(2):389-403. Epub Jul. 16, 2009.

Tomida et al., Usp46 is a quantitative trait gene regulating mouse immobile behavior in the tail suspension and forced swimming tests. Nat Genet. Jun. 2009;41(6):688-95. Epub May 24, 2009.

Truitt et al., 1,2-Disubstituted naphth[2,3-d]imidazole-4,9-diones and corresponding quaternary salts. J Med Chem. 1964;7(3):362-4.

Ungwitayatorn et al., Synthesis and HIV-1 Reverse Transcriptase Inhibitory Activity of Non-Nucleoside Phthalimide Derivatives. Chinese Journal of Chemistry. Feb. 2008;26(2):379-87.

Van Der Horst et al., FOXO4 transcriptional activity is regulated by monoubiquitination and USP7/HAUSP. Nat Cell Biol. Oct. 2006;8(10):1064-73. Epub Sep. 10, 2006.

Vanelle et al., Preparation and in vitro antiprotozoan activity of new naphthoimidazolediones. European Journal of Med Chem. Jun. 1997;32(6):523-28.

Wang et al., [1,1'-Bis(diphenylphosphino)ferrocene]dichloropalladium/1,1'-bis(diphenylphosphino)ferrocene catalyzed synthesis of 2,3-diamino-1,4-naphthoquinones. Synthesis. 2007. 7:989-98.

Whisstock et al., Prediction of protein function from protein sequence and structure. Q Rev Biophys. Aug. 2003;36(3):307-40.

Wishart et al., A single mutation converts a novel phosphotyrosine binding domain into a dual-specificity phosphatase. J Biol Chem. Nov. 10, 1995;270(45):26782-5.

Wong et al., Structural alterations of the epidermal growth factor receptor gene in human gliomas. Proc Natl Acad Sci U S A. Apr. 1, 1992;89(7):2965-9.

Yang et al., Regulation of the Fanconi anemia pathway by a SUMO-like delivery network. Genes Dev. Sep. 1, 2011;25(17):1847-58.

Yang et al., Targeted disruption of the murine Fanconi anemia gene, Fancg/Xrcc9. Blood. Dec. 1, 2001;98(12):3435-40.

Yao et al., Proteasome recruitment and activation of the Uch37 deubiquitinating enzyme by Adrm1. Nat Cell Biol. Sep. 2006;8(9):994-1002. Epub Aug. 13, 2006.

Zhang et al., A Simple Statistical Parameter for Use in Evaluation and Validation of High Throughput Screening Assays. J Biomol Screen. 1999;4(2):67-73.

\* cited by examiner

Figure 8   A.   B.
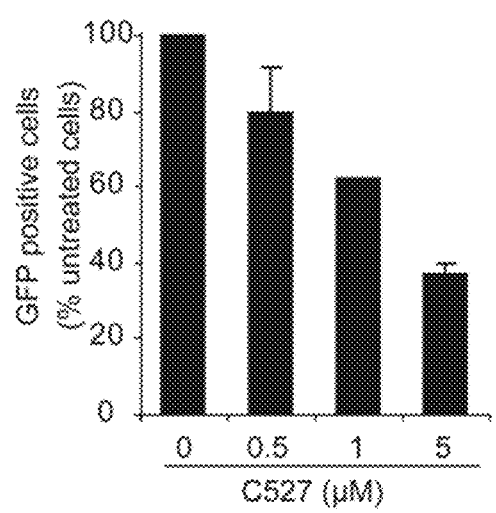
HR
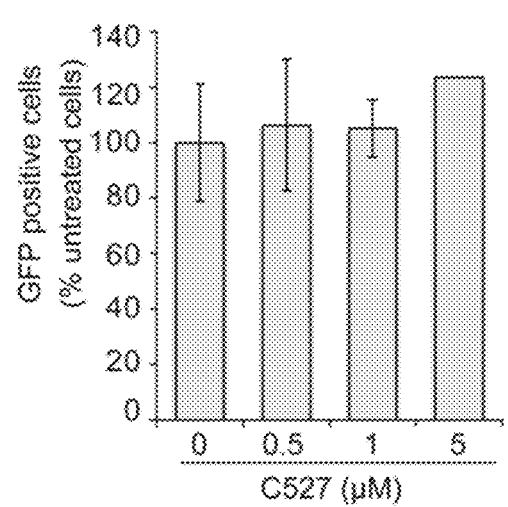
NHEJ

```
                            SEQUENCE LISTING

<160> NUMBER OF SEQ ID NOS: 4

<210> SEQ ID NO 1
<211> LENGTH: 76
<212> TYPE: PRT
<213> ORGANISM: Homo sapiens

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45
```

```
Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 2
<211> LENGTH: 785
<212> TYPE: PRT
<213> ORGANISM: Homo sapiens

<400> SEQUENCE: 2

Met Pro Gly Val Ile Pro Ser Glu Ser Asn Gly Leu Ser Arg Gly Ser
1               5                   10                  15

Pro Ser Lys Lys Asn Arg Leu Ser Leu Lys Phe Phe Gln Lys Lys Glu
            20                  25                  30

Thr Lys Arg Ala Leu Asp Phe Thr Asp Ser Gln Glu Asn Glu Glu Lys
        35                  40                  45

Ala Ser Glu Tyr Arg Ala Ser Glu Ile Asp Gln Val Val Pro Ala Ala
    50                  55                  60

Gln Ser Ser Pro Ile Asn Cys Glu Lys Arg Glu Asn Leu Leu Pro Phe
65                  70                  75                  80

Val Gly Leu Asn Asn Leu Gly Asn Thr Cys Tyr Leu Asn Ser Ile Leu
                85                  90                  95

Gln Val Leu Tyr Phe Cys Pro Gly Phe Lys Ser Gly Val Lys His Leu
            100                 105                 110

Phe Asn Ile Ile Ser Arg Lys Lys Glu Ala Leu Lys Asp Glu Ala Asn
        115                 120                 125

Gln Lys Asp Lys Gly Asn Cys Lys Glu Asp Ser Leu Ala Ser Tyr Glu
    130                 135                 140

Leu Ile Cys Ser Leu Gln Ser Leu Ile Ile Ser Val Glu Gln Leu Gln
145                 150                 155                 160

Ala Ser Phe Leu Leu Asn Pro Glu Lys Tyr Thr Asp Glu Leu Ala Thr
                165                 170                 175

Gln Pro Arg Arg Leu Leu Asn Thr Leu Arg Glu Leu Asn Pro Met Tyr
            180                 185                 190

Glu Gly Tyr Leu Gln His Asp Ala Gln Glu Val Leu Gln Cys Ile Leu
        195                 200                 205

Gly Asn Ile Gln Glu Thr Cys Gln Leu Leu Lys Lys Glu Glu Val Lys
    210                 215                 220

Asn Val Ala Glu Leu Pro Thr Lys Val Glu Glu Ile Pro His Pro Lys
225                 230                 235                 240

Glu Glu Met Asn Gly Ile Asn Ser Ile Glu Met Asp Ser Met Arg His
                245                 250                 255

Ser Glu Asp Phe Lys Glu Lys Leu Pro Lys Gly Asn Gly Lys Arg Lys
            260                 265                 270

Ser Asp Thr Glu Phe Gly Asn Met Lys Lys Lys Val Lys Leu Ser Lys
        275                 280                 285

Glu His Gln Ser Leu Glu Glu Asn Gln Arg Gln Thr Arg Ser Lys Arg
    290                 295                 300

Lys Ala Thr Ser Asp Thr Leu Glu Ser Pro Pro Lys Ile Ile Pro Lys
305                 310                 315                 320

Tyr Ile Ser Glu Asn Glu Ser Pro Arg Pro Ser Gln Lys Lys Ser Arg
                325                 330                 335
```

-continued

Val Lys Ile Asn Trp Leu Lys Ser Ala Thr Lys Gln Pro Ser Ile Leu
            340                 345                 350

Ser Lys Phe Cys Ser Leu Gly Lys Ile Thr Thr Asn Gln Gly Val Lys
            355                 360                 365

Gly Gln Ser Lys Glu Asn Glu Cys Asp Pro Glu Glu Asp Leu Gly Lys
    370                 375                 380

Cys Glu Ser Asp Asn Thr Thr Asn Gly Cys Gly Leu Glu Ser Pro Gly
385                 390                 395                 400

Asn Thr Val Thr Pro Val Asn Val Asn Glu Val Lys Pro Ile Asn Lys
                405                 410                 415

Gly Glu Glu Gln Ile Gly Phe Glu Leu Val Lys Leu Phe Gln Gly
            420                 425                 430

Gln Leu Val Leu Arg Thr Arg Cys Leu Glu Cys Glu Ser Leu Thr Glu
            435                 440                 445

Arg Arg Glu Asp Phe Gln Asp Ile Ser Val Pro Val Gln Glu Asp Glu
    450                 455                 460

Leu Ser Lys Val Glu Glu Ser Ser Glu Ile Ser Pro Glu Pro Lys Thr
465                 470                 475                 480

Glu Met Lys Thr Leu Arg Trp Ala Ile Ser Gln Phe Ala Ser Val Glu
                485                 490                 495

Arg Ile Val Gly Glu Asp Lys Tyr Phe Cys Glu Asn Cys His His Tyr
            500                 505                 510

Thr Glu Ala Glu Arg Ser Leu Leu Phe Asp Lys Met Pro Glu Val Ile
            515                 520                 525

Thr Ile His Leu Lys Cys Phe Ala Ala Ser Gly Leu Glu Phe Asp Cys
            530                 535                 540

Tyr Gly Gly Leu Ser Lys Ile Asn Thr Pro Leu Leu Thr Pro Leu
545                 550                 555                 560

Lys Leu Ser Leu Glu Glu Trp Ser Thr Lys Pro Thr Asn Asp Ser Tyr
                565                 570                 575

Gly Leu Phe Ala Val Val Met His Ser Gly Ile Thr Ile Ser Ser Gly
            580                 585                 590

His Tyr Thr Ala Ser Val Lys Val Thr Asp Leu Asn Ser Leu Glu Leu
            595                 600                 605

Asp Lys Gly Asn Phe Val Val Asp Gln Met Cys Glu Ile Gly Lys Pro
    610                 615                 620

Glu Pro Leu Asn Glu Glu Ala Arg Gly Val Val Glu Asn Tyr Asn
625                 630                 635                 640

Asp Glu Glu Val Ser Ile Arg Val Gly Gly Asn Thr Gln Pro Ser Lys
                645                 650                 655

Val Leu Asn Lys Lys Asn Val Glu Ala Ile Gly Leu Leu Gly Gly Gln
            660                 665                 670

Lys Ser Lys Ala Asp Tyr Glu Leu Tyr Asn Lys Ala Ser Asn Pro Asp
    675                 680                 685

Lys Val Ala Ser Thr Ala Phe Ala Glu Asn Arg Asn Ser Glu Thr Ser
            690                 695                 700

Asp Thr Thr Gly Thr His Glu Ser Asp Arg Asn Lys Glu Ser Ser Asp
705                 710                 715                 720

Gln Thr Gly Ile Asn Ile Ser Gly Phe Glu Asn Lys Ile Ser Tyr Val
                725                 730                 735

Val Gln Ser Leu Lys Glu Tyr Glu Gly Lys Trp Leu Leu Phe Asp Asp
            740                 745                 750

-continued

```
Ser Glu Val Lys Val Thr Glu Lys Asp Phe Leu Asn Ser Leu Ser
            755                 760                 765

Pro Ser Thr Ser Pro Thr Ser Thr Pro Tyr Leu Leu Phe Tyr Lys Lys
    770                 775                 780

Leu
785

<210> SEQ ID NO 3
<211> LENGTH: 677
<212> TYPE: PRT
<213> ORGANISM: Homo sapiens

<400> SEQUENCE: 3

Met Ala Ala His His Arg Gln Asn Thr Ala Gly Arg Arg Lys Val Gln
1               5                   10                  15

Val Ser Tyr Val Ile Arg Asp Glu Val Glu Lys Tyr Asn Arg Asn Gly
            20                  25                  30

Val Asn Ala Leu Gln Leu Asp Pro Ala Leu Asn Arg Leu Phe Thr Ala
        35                  40                  45

Gly Arg Asp Ser Ile Ile Arg Ile Trp Ser Val Asn Gln His Lys Gln
    50                  55                  60

Asp Pro Tyr Ile Ala Ser Met Glu His His Thr Asp Trp Val Asn Asp
65                  70                  75                  80

Ile Val Leu Cys Cys Asn Gly Lys Thr Leu Ile Ser Ala Ser Ser Asp
                85                  90                  95

Thr Thr Val Lys Val Trp Asn Ala His Lys Gly Phe Cys Met Ser Thr
            100                 105                 110

Leu Arg Thr His Lys Asp Tyr Val Lys Ala Leu Ala Tyr Ala Lys Asp
        115                 120                 125

Lys Glu Leu Val Ala Ser Ala Gly Leu Asp Arg Gln Ile Phe Leu Trp
    130                 135                 140

Asp Val Asn Thr Leu Thr Ala Leu Thr Ala Ser Asn Asn Thr Val Thr
145                 150                 155                 160

Thr Ser Ser Leu Ser Gly Asn Lys Asp Ser Ile Tyr Ser Leu Ala Met
                165                 170                 175

Asn Gln Leu Gly Thr Ile Ile Val Ser Gly Ser Thr Glu Lys Val Leu
            180                 185                 190

Arg Val Trp Asp Pro Arg Thr Cys Ala Lys Leu Met Lys Leu Lys Gly
        195                 200                 205

His Thr Asp Asn Val Lys Ala Leu Leu Leu Asn Arg Asp Gly Thr Gln
    210                 215                 220

Cys Leu Ser Gly Ser Ser Asp Gly Thr Ile Arg Leu Trp Ser Leu Gly
225                 230                 235                 240

Gln Gln Arg Cys Ile Ala Thr Tyr Arg Val His Asp Glu Gly Val Trp
                245                 250                 255

Ala Leu Gln Val Asn Asp Ala Phe Thr His Val Tyr Ser Gly Gly Arg
            260                 265                 270

Asp Arg Lys Ile Tyr Cys Thr Asp Leu Arg Asn Pro Asp Ile Arg Val
        275                 280                 285

Leu Ile Cys Glu Glu Lys Ala Pro Val Leu Lys Met Glu Leu Asp Arg
    290                 295                 300

Ser Ala Asp Pro Pro Ala Ile Trp Val Ala Thr Thr Lys Ser Thr
305                 310                 315                 320

Val Asn Lys Trp Thr Leu Lys Gly Ile His Asn Phe Arg Ala Ser Gly
                325                 330                 335
```

Asp Tyr Asp Asn Asp Cys Thr Asn Pro Ile Thr Pro Leu Cys Thr Gln
            340                 345                 350

Pro Asp Gln Val Ile Lys Gly Gly Ala Ser Ile Ile Gln Cys His Ile
            355                 360                 365

Leu Asn Asp Lys Arg His Ile Leu Thr Lys Asp Thr Asn Asn Val
    370                 375                 380

Ala Tyr Trp Asp Val Leu Lys Ala Cys Lys Val Glu Asp Leu Gly Lys
385                 390                 395                 400

Val Asp Phe Glu Asp Glu Ile Lys Lys Arg Phe Lys Met Val Tyr Val
                405                 410                 415

Pro Asn Trp Phe Ser Val Asp Leu Lys Thr Gly Met Leu Thr Ile Thr
            420                 425                 430

Leu Asp Glu Ser Asp Cys Phe Ala Ala Trp Val Ser Ala Lys Asp Ala
    435                 440                 445

Gly Phe Ser Ser Pro Asp Gly Ser Asp Pro Lys Leu Asn Ile Gly Gly
            450                 455                 460

Leu Leu Leu Gln Ala Leu Leu Glu Tyr Trp Pro Arg Thr His Val Asn
465                 470                 475                 480

Pro Met Asp Glu Glu Asn Glu Val Asn His Val Asn Gly Glu Gln
                485                 490                 495

Glu Asn Arg Val Gln Lys Gly Asn Gly Tyr Phe Gln Val Pro Pro His
                500                 505                 510

Thr Pro Val Ile Phe Gly Glu Ala Gly Gly Arg Thr Leu Phe Arg Leu
            515                 520                 525

Leu Cys Arg Asp Ser Gly Gly Glu Thr Glu Ser Met Leu Leu Asn Glu
    530                 535                 540

Thr Val Pro Gln Trp Val Ile Asp Ile Thr Val Asp Lys Asn Met Pro
545                 550                 555                 560

Lys Phe Asn Lys Ile Pro Phe Tyr Leu Gln Pro His Ala Ser Ser Gly
                565                 570                 575

Ala Lys Thr Leu Lys Lys Asp Arg Leu Ser Ala Ser Asp Met Leu Gln
            580                 585                 590

Val Arg Lys Val Met Glu His Val Tyr Glu Lys Ile Ile Asn Leu Asp
    595                 600                 605

Asn Glu Ser Gln Thr Thr Ser Ser Ser Asn Asn Glu Lys Pro Gly Glu
610                 615                 620

Gln Glu Lys Glu Glu Asp Ile Ala Val Leu Ala Glu Lys Ile Glu
625                 630                 635                 640

Leu Leu Cys Gln Asp Gln Val Leu Asp Pro Asn Met Asp Leu Arg Thr
                645                 650                 655

Val Lys His Phe Ile Trp Lys Ser Gly Gly Asp Leu Thr Leu His Tyr
            660                 665                 670

Arg Gln Lys Ser Thr
        675

<210> SEQ ID NO 4
<211> LENGTH: 261
<212> TYPE: PRT
<213> ORGANISM: Homo sapiens

<400> SEQUENCE: 4

Met Phe Glu Ala Arg Leu Val Gln Gly Ser Ile Leu Lys Lys Val Leu
1               5                   10                  15

Glu Ala Leu Lys Asp Leu Ile Asn Glu Ala Cys Trp Asp Ile Ser Ser

```
                    20                  25                  30
Ser Gly Val Asn Leu Gln Ser Met Asp Ser Ser His Val Ala Leu Val
            35                  40                  45
Gln Leu Thr Leu Arg Ser Glu Gly Phe Asp Thr Tyr Arg Cys Asp Arg
    50                  55                  60
Asn Leu Ala Met Gly Val Asn Leu Thr Ser Met Ser Lys Ile Leu Lys
65                  70                  75                  80
Cys Ala Gly Asn Glu Asp Ile Ile Thr Leu Arg Ala Glu Asp Asn Ala
                85                  90                  95
Asp Thr Leu Ala Leu Val Phe Glu Ala Pro Asn Gln Glu Lys Val Ser
                100                 105                 110
Asp Tyr Glu Met Lys Leu Met Asp Leu Asp Val Glu Gln Ile Gly Ile
            115                 120                 125
Pro Glu Gln Glu Tyr Ser Cys Val Val Lys Met Pro Ser Gly Glu Phe
    130                 135                 140
Ala Arg Ile Cys Arg Asp Leu Ser His Ile Gly Asp Ala Val Val Ile
145                 150                 155                 160
Ser Cys Ala Lys Asp Gly Val Lys Phe Ser Ala Ser Gly Glu Leu Gly
                165                 170                 175
Asn Gly Asn Ile Lys Leu Ser Gln Thr Ser Asn Val Asp Lys Glu Glu
                180                 185                 190
Glu Ala Val Thr Ile Glu Met Asn Glu Pro Val Gln Leu Thr Phe Ala
            195                 200                 205
Leu Arg Tyr Leu Asn Phe Phe Thr Lys Ala Thr Pro Leu Ser Ser Thr
    210                 215                 220
Val Thr Leu Ser Met Ser Ala Asp Val Pro Leu Val Val Glu Tyr Lys
225                 230                 235                 240
Ile Ala Asp Met Gly His Leu Lys Tyr Tyr Leu Ala Pro Lys Ile Glu
                245                 250                 255
Asp Glu Glu Gly Ser
            260
```

SMALL MOLECULE INHIBITORS OF USP1 DEUBIQUITINATING ENZYME ACTIVITY

RELATED APPLICATIONS

This application is a divisional of U.S. application Ser. No. 13/695,036, filed Jun. 17, 2013, which is a national stage filing under 35 U.S.C. § 371 of international application PCT/US2011/034514, filed Apr. 29, 2011, which was published under PCT Article 21(2) in English, which claims the benefit under 35 U.S.C. § 119(e) of U.S. provisional application Ser. No. 61/329,984, filed Apr. 30, 2010, the disculosure of each referenced application is incorporated by reference herein in its entirety.

GOVERNMENT SUPPORT

This invention was made with government support under grant numbers R01 DK043889, R01 HL052725, P01 CA092584, and U19 AI067751 awarded by the National Institutes of Health. The government has certain rights in the invention.

BACKGROUND OF THE INVENTION

Ubiquitin is a small protein consisting of 76 amino acids that is important in the regulation of protein function in the cell. Ubiquitination and deubiquitination are enzymatically mediated processes by which ubiquitin is covalently bound to or unbound from a target protein. These processes have been implicated in the regulation of the cell cycle, apoptosis, the marking of transmembrane proteins such as receptors for removal, regulation of DNA transcription and repair, and other important functions. Proteins are targeted for degradation by the proteasome in the cell by being "tagged" with three or more ubiquitin molecules (polyubiquitination). The binding of a single ubiquitin molecule (monoubiquitination) does not generally target the monoubiquitinated protein for degradation. Rather, it may trigger activities such as DNA repair and gene silencing, among other functions. Huang and D'Andrea (2006) *Mol Cell Biol.* 7:323-34.

Deubiquitination allows ubiquitin to be recycled and restores the function of the deubiquitinated proteins. Ubiquitin molecules are cleaved from a protein by deubiquitinating enzymes, which are cysteine proteases that operate through an active site thiol. There are approximately 95 different deubiquitinating enzymes in human cells. Huang et al. (2006) *Nature Cell Biol.* 8(4):339-47. Among them, Ubiquitin Specific Protease 1 (USP1), also known as ubiquitin specific peptidase 1 and as ubiquitin carboxyl terminal hydrolase 1, has been found to regulate the repair of DNA damage induced by DNA cross-linking agents, which include agents such as cisplatin, mitomycin C (MMC), diepoxybutane (DEB), ionizing radiation (IR), and ultraviolet (UV) radiation.

USP1 has been shown to deubiquitinate monoubiquitinated Fanconi anemia group complementation group D2 (FANCD2-Ub), a protein that in its monoubiquitinated form mediates DNA repair from the damage induced by the aforementioned agents. Nijman et al. (2005) *Mol Cell* 17:331-39. USP1 also has been shown to deubiquitinate monoubiquitinated proliferating cell nuclear antigen (PCNA-Ub), a protein that in its monoubiquitinated form activates DNA translesion synthesis, a polymerase-mediated bypass of DNA lesions. Huang et al. (2006) *Nature Cell Biol.* 8(4):339-47.

Recently it was reported that USP1 forms a complex with and is activated by USP1 associated factor 1 (UAF1), also known as WD repeat domain 48. Cohn et al. (2007) Mol Cell 28:786-97; US 2008/0167229 A1. The active USP1/UAF1 complex controls cellular levels of monubiquitinated FANCD2. Even more recently, it was reported that UAF1 also separately forms complexes with and activates two additional deubiquitinating enzymes, ubiquitin specific protease 12 (USP12) and ubiquitin specific protease 46 (USP46). Cohn et al. (2009) *J Biol Chem.* 284(8):5343-51.

Co-owned US 2008/0167229 discloses three compounds, β-lapachone, Biomol AP401 (propidium iodide), and RK-682, as potential small molecule inhibitors of USP1/UAF1 complex-mediated deubiquitinase activity.

SUMMARY OF THE INVENTION

The invention provides certain small molecule inhibitors of USP1 activity as well as compositions and methods related to the inhibitors useful for the inhibition of USP1 activity in vitro and in vivo. These small molecule inhibitors of USP1 activity are structurally distinct from β-lapachone, Biomol AP401 (propidium iodide), and RK-682. The invention further provides, in part, compositions and methods useful for the treatment, prevention, and characterization of cancer based on the ability to inhibit USP1 activity in cancer cells.

It has surprisingly been discovered according to the present invention that inhibition of USP1 activity, which inhibits deubiquitination of monoubiquitinated FANCD2 (FANCD2-Ub), results in reduced DNA repair activity in cells, including cancer cells. This was unexpected because FANCD2-Ub is the active form of FANCD2. Inhibition of USP1 activity thus can render cancer cells, including cancer cells otherwise resistant to treatment with DNA cross-linking agents, susceptible to treatment with DNA cross-linking agents.

The deubiquitinating enzyme USP1 and its associated factor UAF1 regulate the Fanconi Anemia (FA)-BRCA DNA repair pathway by catalyzing the deubiquitination of mono-ubiquitinated FANCD2. Inactivation of USP1/UAF1 results in elevated level of mono-ubiquitinated FANCD2, disruption of the FA-BRCA pathway, and cellular hypersensitivity to DNA crosslinking agents, such as mitomycin C and cisplatin. Targeting USP1/UAF1 with a small-molecule inhibitor therefore enhances the efficacy of DNA crosslinking agents in cancer therapy.

An aspect of the invention is a pharmaceutical composition including a small molecule inhibitor of ubiquitin specific protease 1 (USP1) according to Formula I:

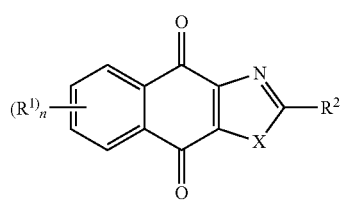

Formula I wherein
X is O, S, or $NR^3$;
n is 0, 1, 2, 3, or 4;
each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^A$; —$C(=O)R^A$; —$C(=O)N(R^A)_2$; —$CO_2R^A$; —CN; —SCN; —$SR^A$; —$SOR^A$; —$SO_2R^A$; —$NO_2$; —$N_3$; —$N(R^A)_2$; —$NHC(=O)R^A$; —$NR^AC(=O)N(R_A)_2$; —$OC(=O)OR^A$; —$OC(=O)R^A$; —$OC(=O)N(R^A)_2$; —$NR^AC(=O)OR^A$; or —$C(R^A)_3$; wherein each occurrence of $R^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^B$; —$C(=O)R^B$; —$C(=O)N(R^B)_2$; —$CO_2R^B$; —CN; —SCN; —$SR^B$; —$SOR^B$; —$SO_2R^B$; —$NO_2$; —$N_3$; —$N(R^B)_2$; —$NHC(=O)R^B$; —$NR^BC(=O)N(R^B)_2$; —$OC(=O)OR^B$; —$OC(=O)R^B$; —$OC(=O)N(R^B)_2$; —$NR^BC(=O)OR^B$; or —$C(R^B)_3$; wherein each occurrence of $R^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^3$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

or a pharmaceutically acceptable salt thereof, and a pharmaceutically acceptable carrier.

In one embodiment according to this and other aspects of the invention, the small molecule inhibitor of USP1 according to Formula I is the compound of Formula IV (527):

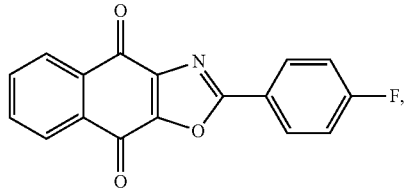

Formula IV (527)

or a pharmaceutically acceptable salt thereof.

In one embodiment the pharmaceutical composition further includes a DNA cross-linking agent, for example chemotherapeutic agents including alkylating agents, cisplatin, and mitomycin C.

In one embodiment the pharmaceutical composition further includes a poly (adenosine diphosphate (ADP)-ribose) polymerase (PARP) inhibitor.

An aspect of the invention is a pharmaceutical composition including a small molecule inhibitor of USP1 according to Formula II:

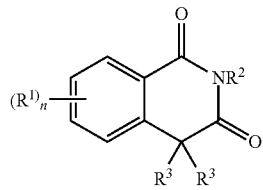

Formula II wherein n is 0, 1, 2, 3, or 4;

each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^A$; —$C(=O)R^A$; —$CO_2R^A$; —$C(=O)N(R^A)_2$; —CN; —SCN; —$SR^A$; —$SOR^A$; —$SO_2R^A$; —$NO_2$; —$N_3$; —$N(R^A)_2$; —$NHC(=O)R^A$; —$NR^AC(=O)N(R_A)_2$; —$OC(=O)OR^A$; —$OC(=O)R^A$; —$OC(=O)N(R^A)_2$; —$NR^AC(=O)OR^A$; or —$C(R^A)_3$; wherein each occurrence of $R^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^2$ is hydrogen; a nitrogen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$C(=O)R^B$; —$C(=O)N(R^B)_2$; —$CO_2R^B$; or —$C(R^B)_3$; wherein each occurrence of $R^B$ is independently a hydrogen, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

each occurrence of $R^3$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^C$; —$C(=O)R^C$; —$C(=O)N(R^C)_2$; —$CO_2R^C$; —CN; —SCN; —$SR^C$; —$SOR^C$; —$SO_2R^C$; —$NO_2$; —$N_3$; —$N(R^C)_2$; —$NHC(=O)R^C$; —$NR^CC(=O)N(R^C)_2$; —$OC(=O)OR^C$; —$OC(=O)R^C$; —$OC(=O)N(R^C)_2$; —$NR^CC(=O)OR^C$; or —$C(R^C)_3$; wherein each occurrence of $R^C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; wherein both occurrences of $R^3$ may optionally be taken together with the intervening carbon atoms to form an optionally substituted cyclic moiety or may be =O, =S, or =$NR^C$;

or a pharmaceutically acceptable salt thereof, and a pharmaceutically acceptable carrier.

In one embodiment according to this and other aspects of the invention, the small molecule inhibitor of USP1 according to Formula II is the compound of Formula V (947):

Formula V (947)

[Chemical structure of Formula V (947)]

or a pharmaceutically acceptable salt thereof.

In one embodiment the pharmaceutical composition further includes a DNA cross-linking agent, for example chemotherapeutic agents including alkylating agents, cisplatin, and mitomycin C.

In one embodiment the pharmaceutical composition further includes a PARP inhibitor.

An aspect of the invention is a pharmaceutical composition including (a) a small molecule inhibitor of USP1 according to Formula III (933):

Formula III (933)

[Chemical structure of Formula III (933)]

or a pharmaceutically acceptable salt thereof, (b) a DNA cross-linking agent, and (c) a pharmaceutically acceptable carrier.

An aspect of the invention is a pharmaceutical composition including (a) a small molecule inhibitor of USP1 according to Formula III (933):

Formula III (933)

[Chemical structure of Formula III (933)]

or a pharmaceutically acceptable salt thereof, (b) a PARP inhibitor, and (c) a pharmaceutically acceptable carrier.

In one embodiment, any of foregoing pharmaceutical compositions is formulated for targeted delivery to a cancer cell.

In another aspect the invention is a method for inhibiting USP1-mediated deubiqitination of a ubiquitinated substrate. The method includes the step of contacting the ubiquitinated substrate with a small molecule inhibitor of USP1 according to Formula I:

Formula I

[Chemical structure of Formula I with $(R^1)_n$, $R^2$, X]

as set forth above, or a pharmaceutically acceptable salt thereof, in an amount effective to inhibit USP1-mediated deubiqitination of the ubiquitinated substrate.

An aspect of the invention is a method for inhibiting USP1-mediated deubiqitination of a ubiquitinated substrate. The method includes the step of contacting the ubiquitinated substrate with a small molecule inhibitor of USP1 according to Formula II:

Formula II

[Chemical structure of Formula II with $(R^1)_n$, $NR^2$, $R^3$ $R^3$]

as set forth above, or a pharmaceutically acceptable salt thereof, in an amount effective to inhibit USP1-mediated deubiqitination of the ubiquitinated substrate.

An aspect of the invention is a method for inhibiting USP1-mediated deubiqitination of a ubiquitinated substrate. The method includes the step of contacting the ubiquitinated substrate with a small molecule inhibitor of USP1 according to Formula III (933):

Formula III (933)

[Chemical structure of Formula III (933)]

or a pharmaceutically acceptable salt thereof, in an amount effective to inhibit USP1-mediated deubiqitination of the ubiquitinated substrate.

An aspect of the invention is a method for treating a subject having a cancer. The method includes the step of administering to a subject having cancer in need of such treatment a small molecule inhibitor of USP1 according to Formula I:

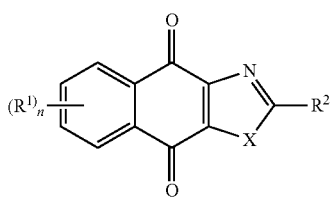

Formula I as set forth above, or a pharmaceutically acceptable salt thereof, in an amount effective to treat the cancer.

In one embodiment the method further includes the step of administering to the subject a DNA cross-linking agent.

In one embodiment the method further includes the step of administering to the subject a PARP inhibitor.

In one embodiment the method further includes the step or steps of administering to the subject a DNA cross-linking agent and a PARP inhibitor.

An aspect of the invention is a method for treating a subject having a cancer. The method includes the step of administering to a subject having cancer in need of such treatment a small molecule inhibitor of USP1 according to Formula II:

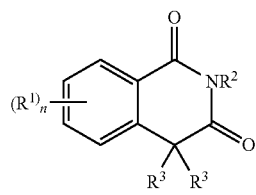

Formula II as set forth above, or a pharmaceutically acceptable salt thereof, in an amount effective to treat the cancer.

In one embodiment the method further includes the step of administering to the subject a DNA cross-linking agent.

In one embodiment the method further includes the step of administering to the subject a PARP inhibitor.

In one embodiment the method further includes the step or steps of administering to the subject a DNA cross-linking agent and a PARP inhibitor.

An aspect of the invention is a method for treating a subject having a cancer. The method includes the step of administering to a subject having cancer in need of such treatment a small molecule inhibitor of ubiquitin specific protease 1 (USP1) according to Formula III:

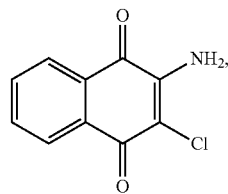

Formula III (933)

or a pharmaceutically acceptable salt thereof, in an amount effective to treat the cancer.

In one embodiment the method further includes the step of administering to the subject a DNA cross-linking agent.

In one embodiment the method further includes the step of administering to the subject a PARP inhibitor.

In one embodiment the method further includes the step or steps of administering to the subject a DNA cross-linking agent and a PARP inhibitor.

An aspect of the invention is a method for sensitizing a cancer to a DNA cross-linking agent. The method includes the step of contacting a cancer with a small molecule inhibitor of USP1 according to Formula I:

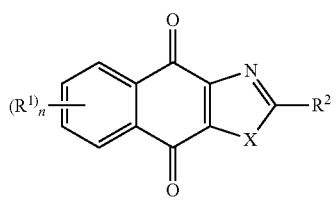

Formula I as set forth above, or a pharmaceutically acceptable salt thereof, in an amount effective to sensitize the cancer to a DNA cross-linking agent.

An aspect of the invention is a method for sensitizing a cancer to a DNA cross-linking agent. The method includes the step of contacting a cancer with a small molecule inhibitor of USP1 according to Formula II:

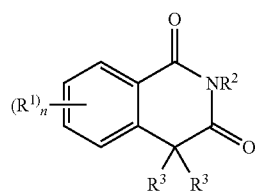

Formula II as set forth above, or a pharmaceutically acceptable salt thereof, in an amount effective to sensitize the cancer to a DNA cross-linking agent.

An aspect of the invention is a method for sensitizing a cancer to a DNA cross-linking agent. The method includes the step of contacting a cancer with a small molecule inhibitor of USP1 according to Formula III (933):

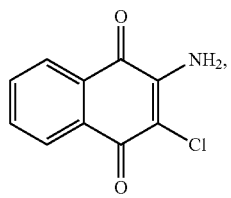

Formula III (933)

or a pharmaceutically acceptable salt thereof, in an amount effective to sensitize the cancer to a DNA cross-linking agent.

An aspect of the invention is a method to identify a cancer that is responsive to USP1 inhibition. The method includes the steps of contacting cancer cells from a cancer with a small molecule inhibitor of USP1 according to Formula I:

Formula I

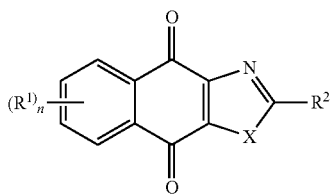

as set forth above, or a pharmaceutically acceptable salt thereof; and measuring USP1 activity in the cancer cells contacted with the small molecule inhibitor of USP1, wherein reduced USP1 activity in the cancer cells contacted with the small molecule inhibitor of USP1 relative to control USP1 activity in the cancer cells not contacted with the small molecule inhibitor of USP1 identifies the cancer as a cancer that that is responsive to USP1 inhibition.

An aspect of the invention is a method to identify a cancer that is responsive to USP1 inhibition. The method includes the steps of contacting cancer cells from a cancer with a small molecule inhibitor of USP1 according to Formula II:

Formula II

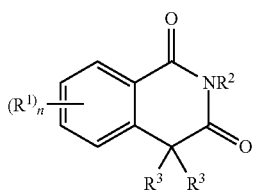

as set forth above, or a pharmaceutically acceptable salt thereof; and measuring USP1 activity in the cancer cells contacted with the small molecule inhibitor of USP1, wherein reduced USP1 activity in the cancer cells contacted with the small molecule inhibitor of USP1 relative to control USP1 activity in the cancer cells not contacted with the small molecule inhibitor of USP1 identifies the cancer as a cancer that that is responsive to USP1 inhibition.

An aspect of the invention is a method to identify a cancer that is responsive to USP1 inhibition. The method includes the steps of contacting cancer cells from a cancer with a small molecule inhibitor of USP1 according to Formula III:

Formula III (933)

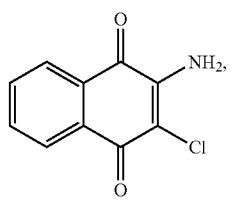

or a pharmaceutically acceptable salt thereof; and measuring USP1 activity in the cancer cells contacted with the small molecule inhibitor of USP1, wherein reduced USP1 activity in the cancer cells contacted with the small molecule inhibitor of USP1 relative to control USP1 activity in the cancer cells not contacted with the small molecule inhibitor of USP1 identifies the cancer as a cancer that that is responsive to USP1 inhibition.

An aspect of the invention is a method to identify a cancer that is responsive to DNA cross-linking therapy together with USP1 inhibition. The method includes the steps of contacting cancer cells from a cancer with a DNA cross-linking agent and a small molecule inhibitor of USP1 according to Formula I:

Formula I

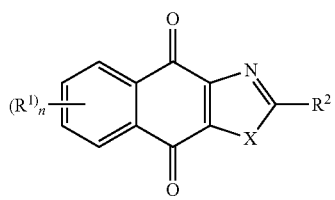

as set forth above, or a pharmaceutically acceptable salt thereof; and measuring proliferation of the cancer cells contacted with the DNA cross-linking agent and the small molecule inhibitor of USP1, wherein reduced proliferation of the cancer cells contacted with the DNA cross-linking agent and the small molecule inhibitor of USP1 relative to control proliferation of the cancer cells contacted with the DNA cross-linking agent but not the small molecule USP1 inhibitor identifies the cancer as a cancer that is responsive to DNA cross-linking therapy together with USP1 inhibition.

An aspect of the invention is a method to identify a cancer that is responsive to DNA cross-linking therapy together with USP1 inhibition. The method includes the steps of contacting cancer cells from a cancer with a DNA cross-linking agent and a small molecule inhibitor of USP1 according to Formula II:

Formula II

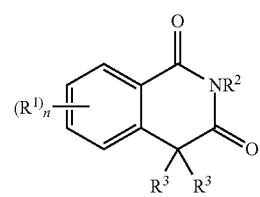

as set forth above, or a pharmaceutically acceptable salt thereof; and measuring proliferation of the cancer cells contacted with the DNA cross-linking agent and the small molecule inhibitor of USP1, wherein reduced proliferation of the cancer cells contacted with the DNA cross-linking agent and the small molecule inhibitor of USP1 relative to control proliferation of the cancer cells contacted with the DNA cross-linking agent but not the small molecule USP1 inhibitor identifies the cancer as a cancer that is responsive to DNA cross-linking therapy together with USP1 inhibition.

An aspect of the invention is a method to identify a cancer that is responsive to DNA cross-linking therapy together with USP1 inhibition. The method includes the steps of contacting cancer cells from a cancer with a DNA cross-linking agent and a small molecule inhibitor of USP1 according to Formula III:

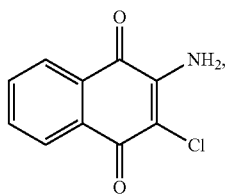

Formula III (933)

or a pharmaceutically acceptable salt thereof; and measuring proliferation of the cancer cells contacted with the DNA cross-linking agent and the small molecule inhibitor of USP1, wherein reduced proliferation of the cancer cells contacted with the DNA cross-linking agent and the small molecule inhibitor of USP1 relative to control proliferation of the cancer cells contacted with the DNA cross-linking agent but not the small molecule USP1 inhibitor identifies the cancer as a cancer that is responsive to DNA cross-linking therapy together with USP1 inhibition.

BRIEF DESCRIPTION OF THE DRAWINGS

FIG. 5A demonstrates that C527 inhibits USP1 activity in a time-dependent manner. Purified USP1/UAF1 complex was incubated with 1 μM C527 or DMSO for indicated time, followed by the addition of Ub-AMC at 0.5 μM final concentration. The fluorescence at 535 nM was measured to indicate the enzymatic activity of USP1. FIG. 5B shows that C527 inhibits USP1 activity in a dose-dependent manner. C527 at indicated concentrations was incubated with USP1/UAF1 for 3 h and the reaction was as described in FIG. 5A. FIG. 5C shows the IC50 of C527 against USP/UAF1 complex.

FIG. 6D is a summary showing the IC50 of C527 against the indicated enzymes.

FIG. 8 is a composite figure showing that C527 inhibits homologous recombination repair. FIG. 8A shows that C527 inhibits DR-GFP reporter for homologous recombination repair activity. U2OS-DRGFP cells were transfected with I-SCE-I and then exposed to C527 at the indicated concentration for 24 h. Cells were then subjected to flow cytometry analysis. The percentage of GFP positive cells was normalized by solvent vehicle treated group. FIG. 8B shows that C527 has minimal inhibition of NHEJ activity. HeLa cells, integrated with the NHEJ reporter, were treated with C527 and analyzed as described in (FIG. 8A).

FIG. 9A shows that C527 causes DNA damage in tumor cells. HeLa cells were treated with C527 at the indicated concentrations for 24 hrs, and cells were subjected to immunoblotting. Mitomycin C (MMC, 1 μM) was used as a positive control. FIG. 9B shows that C527 inhibits the proliferation of tumor cells. HeLa cells were seeded in a 6-well plate and treated with C527 at the indicated concentrations. Cell proliferation was evaluated using a clonogenic assay.

DETAILED DESCRIPTION OF THE INVENTION

Figure 1:
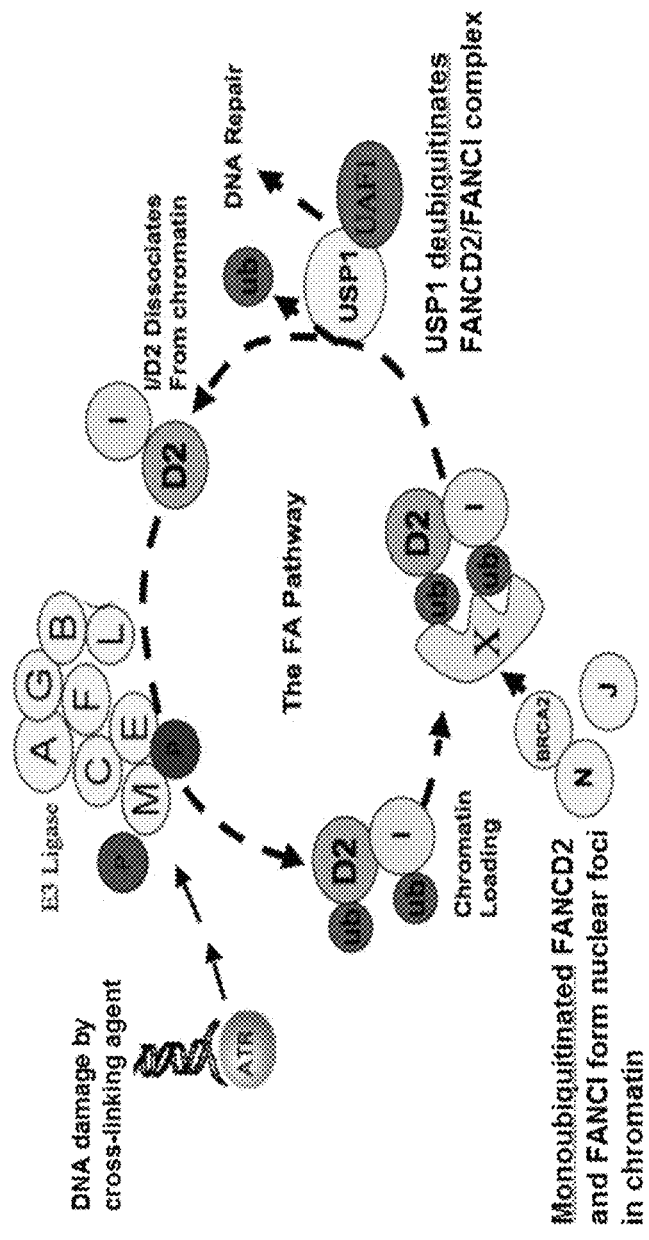
FIG. 1 is a schematic drawing depicting the Fanconi anemia (FA) DNA repair pathway. Ub, ubiquitin; D2, FANCD2; I, FANCI.

The invention is based, at least in part, on the discovery by the instant inventors of certain small molecule inhibitors of USP1 activity. These small molecule inhibitors of USP1 activity inhibit the deubiquitinating activity of USP1, both alone and in combination with UAF1, both in vitro and in vivo. Furthermore, it has now unexpectedly been discovered by the inventors that inhibition of USP1 activity can render cancer cells, including cancer cells otherwise resistant to treatment with DNA cross-linking agents, susceptible to treatment with DNA cross-linking agents.

Ubiquitin is a 76 amino acid protein that can be covalently attached to other proteins, targeting them for degradation or regulating their function. The amino acid sequence of the human form of ubiquitin is given by SEQ ID NO:1:

```
  1    MQIFVKTLTG KTITLEVEPS DTIENVKAKI QDKEGIPPDQ QRLIFAGKQL EDGRTLSDYN
 61    IQKESTLHLV LRLRGG
```

Ubiquitin is covalently attached to other proteins by a ubiquitin transferase enzyme, and it is released from a ubiquitinated protein by a deubiquitinating enzyme.

Ubiquitination and deubiquitination regulate a number of essential biological processes such as gene transcription, DNA replication, and DNA repair. Pickart et al. (2004) *Biochim Biophys Acta* 1695:55-72. Ubiquitin modifications can be divided into three principal types. First, monoubiquitination may alter the activity of the substrate, as has been described for the FANCD2 protein of the Fanconi anemia pathway and the PCNA protein involved in translesion synthesis. Kennedy et al. (2005) *Genes Dev* 19:2925-40; Hoegh et al. (2002) *Nature* 419:135-41. Second, polyubiquitination through K48 linkage typically targets the protein substrate for degradation by the proteasome. Third, polyubiquitination through K63 linkage can alter the activity of the protein substrate by modifying its protein-protein interaction properties.

There are at least 95 putative deubiquitinating enzymes in humans. Nijman et al. (2005) *Cell* 123:773-86. This family of deubiquitinating enzymes is divided into five subfamilies, including the ubiquitin specific protease (USP) subfamily (58 members), the otubain protease (OTU) subfamily and the JAB1/MPN/Mov34 metalloprotease (JAMM) subfamily (14 members each), the Josephine domain protease (MJD) subfamily (5 members), and the ubiquitin C-terminal hydrolase (UCH) subfamily (4 members). The exact biological function for many of these enzymes is currently unknown. However, for those enzymes whose function has been uncovered, it has become apparent that regulation of their activities is essential for integrity of the pathways they regulate.

Ubiquitin-specific protease 1 (USP1) is a cysteine protease with deubiquitinase activity. USP1 cleaves ubiquitin from monoubiquitinated and polyubiquitinated protein substrates, including FANCD2 and PCNA. Huang et al. (2006) *Nature Cell Biol.* 8(4):339-47. The amino acid sequence for the human form of USP1 is given by SEQ ID NO:2:

Fanconi anemia (FA) is a rare chromosome instability syndrome characterized by aplastic anemia in childhood, susceptibility to leukemia and cancer, and hypersensitivity of FA cells to interstrand DNA cross-linking agents such as cisplatin and melphalan. There are thirteen Fanconi anemia genes, and their corresponding proteins fall into several classes of enzymes and structural proteins, including a ubiquitin ligase, monoubiquitinated proteins, a helicase, and one with both helicase and nuclease motifs. Since FA patients share a characteristic clinical and cellular phenotype, it has been assumed that the thirteen FA proteins cooperate in a common DNA repair pathway. Indeed, the FA proteins work in concert to control the monoubiquitinated state of the FANCD2 and FANCI proteins (see FIG. 1) and the downstream functions of the pathway.

As shown in FIG. 1, after DNA damage, the Ataxia Telangiectasia and Rad3-related kinase (ATR) activates FA core complex (FANCA/B/C/E/F/G/L/M). The FA core complex then functions as an E3 ubiquitin ligase and monoubiquitinates FANCD2 and FANCI. The monoubiquitinated FANCD2/FANCI complex is then targeted to chromatin where it forms a complex with additional FA proteins and other DNA repair proteins. A protein complex of USP1 and UAF1 then deubiquitinates FANCD2/FANCI complex, allowing their release from chromatin. USP1 is also required for localization of FANCD2/FANCI into DNA repair foci.

Although mutations in the thirteen FA genes account for most, if not all, cases of FA, additional genes related to the FA-BRCA pathway may also be important. For example, disruption of USP1 in mice yields the FA phenotype, and knockdown of either USP1 or UAF1 also disrupts the FA-BRCA pathway and causes hypersensitivity to DNA cross-linking agents.

USP1 associated factor 1 (UAF1) is a WD repeat endosomal protein that has been described to form a heterodimeric complex with USP1 and thereby to enhance the deubiquitinase activity of USP1. This protein has been previously shown to play a role in the downregulation of the T lymphocyte receptor. Park et al. (2002) *Immunity* 17:221-33. The amino acid sequence for human UAF1 is given by SEQ ID NO:3:

```
  1    MPGVIPSESN GLSRGSPSKK NRLSLKFFQK KETKRALDFT DSQENEEKAS EYRASEIDQV

61    VPAAQSSPIN CEKRENLLPF VGLNNLGNTC YLNSILQVLY FCPGFKSGVK HLFNIISRKK

121    EALKDEANQK DKGNCKEDSL ASYELICSLQ SLIISVEQLQ ASFLLNPEKY TDELATQPRR

181    LLNTLRELNP MYEGYLQHDA QEVLQCILGN IQETCQLLKK EEVKNVAELP TKVEEIPHPK

241    EEMNGINSIE MDSMRHSEDF KEKLPKGNGK RKSDTEFGNM KKKVKLSKEH QSLEENQRQT

301    RSKRKATSDT LESPPKIIPK YISENESPRP SQKKSRVKIN WLKSATKQPS ILSKFCSLGK

361    ITTNQGVKGQ SKENECDPEE DLGKCESDNT TNGCGLESPG NTVTPVNVNE VKPINKGEEQ

421    IGFELVEKLF QGQLVLRTRC LECESLTERR EDFQDISVPV QEDELSKVEE SSEISPEPKT

481    EMKTLRWAIS QFASVERIVG EDKYFCENCH HYTEAERSLL FDKMPEVITI HLKCFAASGL

541    EFDCYGGGLS KINTPLLTPL KLSLEEWSTK PTNDSYGLFA VVMHSGITIS SGHYTASVKV

601    TDLNSLELDK GNFVVDQMCE IGKPEPLNEE EARGVVENYN DEEVSIRVGG NTQPSKVLNK

661    KNVEAIGLLG GQKSKADYEL YNKASNPDKV ASTAFAENRN SETSDTTGTH ESDRNKESSD

721    QTGINISGFE NKISYVVQSL KEYEGKWLLF DDSEVKVTEE KDFLNSLSPS TSPTSTPYLL

781    FYKKL
```

```
  1   MAAHHRQNTA GRRKVQVSYV IRDEVEKYNR NGVNALQLDP ALNRLFTAGR DSIIRIWSVN

61   QHKQDPYIAS MEHHTDWVND IVLCCNGKTL ISASSDTTVK VWNAHKGFCM STLRTHKDYV

121   KALAYAKDKE LVASAGLDRQ IFLWDVNTLT ALTASNNTVT TSSLSGNKDS IYSLAMNQLG

181   TIIVSGSTEK VLRVWDPRTC AKLMKLKGHT DNVKALLLNR DGTQCLSGSS DGTIRLWSLG

241   QQRCIATYRV HDEGVWALQV NDAFTHVYSG GRDRKIYCTD LRNPDIRVLI CEEKAPVLKM

301   ELDRSADPPP AIWVATTKST VNKWTLKGIH NFRASGDYDN DCTNPITPLC TQPDQVIKGG

361   ASIIQCHILN DKRHILTKDT NNNVAYWDVL KACKVEDLGK VDFEDEIKKR FKMVYVPNWF

421   SVDLKTGMLT ITLDESDCFA AWVSAKDAGF SSPDGSDPKL NIGGLLLQAL LEYWPRTHVN

481   PMDEEENEVN HVNGEQENRV QKGNGYFQVP PHTPVIFGEA GGRTLFRLLC RDSGGETESM

541   LLNETVPQWV IDITVDKNMP KFNKIPFYLQ PHASSGAKTL KKDRLSASDM LQVRKVMEHV

601   YEKIINLDNE SQTTSSSNNE KPGEQEKEED IAVLAEEKIE LLCQDQVLDP NMDLRTVKHF

661   IWKSGGDLTL HYRQKST
```

Proliferating cell nuclear antigen (PCNA) is a DNA replication sliding clamp protein that can form part of a DNA polymerase complex. Upon monoubiquitination, PCNA can interact with any of several different DNA polymerases to form a complex which carries out either DNA replication or DNA repair, particularly translesion DNA synthesis. Huang & D'Andrea (2006) *Mol Cell Biol.* 7:323-34. As used herein, "translesion DNA synthesis" is a form of DNA repair in which specialized, damage-tolerant DNA polymerases (such as Pol eta) bypass DNA lesions that would normally stall replication of a DNA strand, allowing for later repair of the bypassed lesion. These DNA lesions can occur upon cellular exposure to ionizing radiation, ultraviolet light, or DNA-disrupting chemical agents. The amino acid sequence of the human form of PCNA is given by SEQ ID NO:4:

```
  1   MFEARLVQGS ILKKVLEALK DLINEACWDI SSSGVNLQSM DSSHVALVQL TLRSEGFDTY

61   RCDRNLAMGV NLTSMSKILK CAGNEDIITL RAEDNADTLA LVFEAPNQEK VSDYEMKLMD

121   LDVEQIGIPE QEYSCVVKMP SGEFARICRD LSHIGDAVVI SCAKDGVKFS ASGELGNGNI

181   KLSQTSNVDK EEEAVTIEMN EPVQLTFALR YLNFFTKATP LSSTVTLSMS ADVPLVVEYK

241   IADMGHLKYY LAPKIEDEEG S
```

Using an initial in vitro screening assay described in the Examples, certain small molecule inhibitors of USP1 were identified from a library of approximately 150,000 compounds. Small molecule inhibitors of USP1 so identified include the compounds of Formula III (933), Formula IV (527), Formula V (947), and Formula VI (009).

-continued

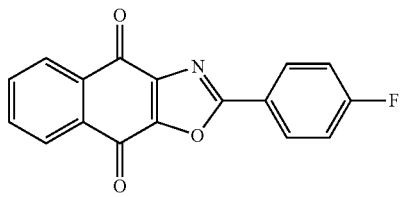

Formula IV (527)

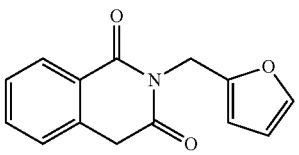

Formula V (947)

-continued

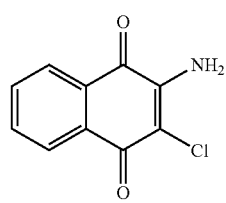

Formula III (933)

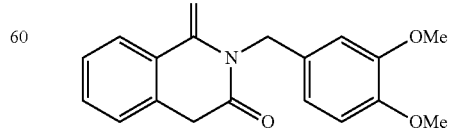

Formula VI (009)

The compounds of Formula IV and V are disclosed herein as representative examples of individual classes of compounds according to Formula I (and related Formula IA) and Formula II, respectively (see below).

As used herein, an "inhibitor of USP1" refers to an agent that decreases deubiquitinase activity of USP1. As used herein, the term "deubiquitinase activity of USP1" and, equivalently, "USP1 activity", refers to the action of USP1 to remove ubiquitin from a ubiquitinated substrate. Deubiquitinase activity can be measured in vitro or in vivo, and it can be measured directly or indirectly. Deubiquitinase activity can be measured by a number of assays including assays that measure the deubiquitination of FANCD2-Ub or PCNA-Ub, natural targets of USP1 deubiquitination. Alternatively, deubiquitinase activity of USP1 can be determined by measuring the deubiquitination of a test molecule such as ubiquitin-7-amido-4-methylcoumarin (AMC-Ub), which produces a fluorescently detectable signal upon the cleavage of ubiquitin. A USP1 polypeptide is deemed to have deubiquitinase activity where the level of deubiquitinated FANCD2, PCNA, or AMC in the presence of USP1 is at least 10% greater than the level of deubiquitinated FANCD2, PCNA, or AMC from a control sample (e.g., sample from the same tissue, or a separate aliquot of a cellular sample) in the absence of USP1. Alternatively a USP1 polypeptide is deemed to have deubiquitinase activity where the level of ubiquitinated FANCD2-Ub, PCNA-Ub, or AMC-Ub is decreased by at least 10% in the presence of USP1 relative to a control sample in the absence of USP1. In one embodiment an increase in USP1 activity in response to an agent as used herein refers to any detectable increase in the production of a deubiquitinated substrate (e.g., deubiquitinated AMC) in the presence of the agent relative to in the absence of the agent, such as a 0.5% increase, a 1% increase or decrease, 2%, 3-5%, 5-10%, 10-20%, 20-40%, 40-80%, 90%, or 100% or more increase in the production of a deubiquitinated substrate. In one embodiment a decrease in USP1 activity in response to an agent as used herein refers to any detectable decrease in the production of a deubiquitinated substrate (e.g., deubiquitinated AMC) in the presence of the agent relative to in the absence of the agent, such as a 0.5% decrease, a 1% decrease, 2%, 3-5%, 5-10%, 10-20%, 20-40%, 40-80%, 90%, or 100% decrease in the production of a deubiquitinated substrate.

As used herein, a "small molecule" refers to an organic molecule of molecular weight of less than 1500 Daltons. Small molecules of the invention exclude short interfering RNA or short interfering hairpin RNA.

Short interfering RNA ("siRNA") is a double-stranded RNA molecule that is generally 17 to 25 base pairs in length, one of whose strands contains a sequence (antisense sequence) that is complementary to a segment of a target messenger RNA. siRNA associates with an RNA-induced silencing complex in the cell, which then binds to a complementary region of a target messenger RNA and inactivates it.

Short interfering hairpin RNA ("shRNA") is a ribonucleic acid containing sense and antisense sequences from a target gene connected by a loop; it can be expressed in mammalian cells from a vector. Transcribed shRNA is transported from the nucleus into the cytoplasm, where it is processed, where it can decrease the expression of a gene with complementary sequences by RNA interference (RNAi).

As used herein, RNA interference ("RNAi") refers to a selective intracellular degradation of RNA by means of an RNA-induced silencing complex (RISC). RNAi occurs in cells naturally to remove foreign RNAs (e.g., viral RNAs). RNAi proceeds via fragments cleaved from free double-stranded RNA molecules (such as viral RNA) which direct the degradative mechanism to other similar RNA sequences. Introduction of the double-stranded RNA into a cell triggers the degradation of the double-stranded RNA into shorter siRNA strands. These siRNAs then associate with RNA-induced silencing complexes, leading to the unwinding of the siRNAs into single strands, which then associate with complementary regions of messenger RNA and prevent the expression of the corresponding proteins. The use of synthetic siRNA to "direct RNA interference (RNAi) against expression" of a target gene refers to the reduction of the expression of the target gene by entry of the synthetic siRNA into the natural RNAi mechanism at the same point as natural siRNA created from double-stranded RNA, e.g., viral RNA, would enter that mechanism. That is, synthetic siRNA associate with the RISC, unwind, and then associate with complementary mRNA regions of target transcripts, which are then degraded.

The compounds of Formula III (933) and Formula V (947) are known. For example, a method for synthesizing the compound of Formula V (947) is disclosed in Sondhi et al. (2008) Letts Org Chem 5:51-4, but this reference does not disclose a use for this compound.

In contrast, the compounds of Formula IV (527) and Formula VI (009) appear to be novel compounds.

The invention in one aspect provides the compound of Formula IV (527).

The invention in one aspect provides the compound of Formula VI (009).

The invention provides a pharmaceutical composition that includes (a) a small molecule inhibitor of USP1 selected from the group consisting of a compound of Formula I, a compound of Formula IA, a compound of Formula II, the compound of Formula IV (527), the compound of Formula V (947), and a combination thereof, and (b) a pharmaceutically acceptable carrier. In one embodiment the pharmaceutical composition includes the compound of Formula IV (527) and a pharmaceutically acceptable carrier. In one embodiment the pharmaceutical composition includes the compound of Formula V (947) and a pharmaceutically acceptable carrier.

As used herein, a "pharmaceutically acceptable carrier" refers to one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficacy.

A pharmaceutical composition of the invention can be prepared by placing an effective amount of at least one active agent of the invention, such as a compound of any one of Formulas I-IV, in a pharmaceutically acceptable carrier.

The invention also provides a pharmaceutical composition that includes (a) a small molecule inhibitor of USP1 selected from the group consisting of a compound of Formula I, a compound of Formula IA, a compound of Formula II, the compound of Formula III (933), the compound of Formula IV (527), the compound of Formula V (947), and any combination thereof; (b) a DNA cross-linking agent; and (c) a pharmaceutically acceptable carrier. In one embodiment the small molecule inhibitor of USP1 is the compound of Formula III (933). In one embodiment the small molecule inhibitor of USP1 is the compound of Formula IV (527). In one embodiment the small molecule inhibitor of USP1 is the compound of Formula V (947).

As used herein, a "DNA cross-linking agent" refers to a chemical compound or radiation that induces DNA cross-linking in a cell when applied to the cell. In one embodiment a DNA cross-linking agent is a chemical compound. Such compounds include certain chemotherapeutic agents, such as cisplatin, carboplatin, oxaliplatin, alkylating agents, mitomycin C, as well as certain carcinogenic chemicals, such as diepoxybutane. Cisplatin (cis-diamminedichloroplatinum (II)) and related compounds carboplatin and oxaliplatin forms DNA cross-links as monoadduct, interstrand cross-link, intrastrand cross-link or DNA protein cross-link. Alkylating agents include cyclophosphamide, chlorambucil, melphalan, ifosfamide, uramustine, and bendamustine.

DNA cross-linking radiation includes ionizing radiation and ultraviolet (UV) radiation. Ionizing radiation consists of subatomic particles or electromagnetic waves that are energetic enough to detach electrons from atoms or molecules, ionizing them. The occurrence of ionization depends on the energy of the impinging individual particles or waves. Generally, particles or photons with energies above a few electron volts (eV) are ionizing. Examples of ionizing particles are energetic alpha particles, beta particles, and neutrons. The ability of an electromagnetic wave (photons) to ionize an atom or molecule depends on its frequency. Radiation on the short-wavelength end of the electromagnetic spectrum, such as high frequency ultraviolet, x-rays, and gamma rays, is ionizing. Ionizing radiation comes from radioactive materials, x-ray tubes, and particle accelerators.

The manner of exposure to DNA cross-linking agents can be deliberate or accidental. Examples of deliberate exposure include therapeutic chemotherapy and radiotherapy. Examples of accidental exposure include occupational exposure to chemicals or ionizing radiation, frequent air travel, and nuclear accidents and nuclear warfare.

In one embodiment the pharmaceutical composition includes a DNA cross-linking agent selected from the group consisting of cisplatin, carboplatin, oxaliplatin, an alkylating agent, and mitomycin C. Any combination of such DNA cross-linking agents is also embraced by the invention.

The invention provides a pharmaceutical composition including (a) a small molecule inhibitor of USP1 selected from the group consisting of a compound of Formula I, a compound of Formula IA, a compound of Formula II, the compound of Formula III (933), the compound of Formula IV (527), the compound of Formula V (947), and any combination thereof; (b) a poly (adenosine diphosphate (ADP)-ribose) polymerase (PARP) inhibitor; and (c) a pharmaceutically acceptable carrier. In one embodiment the small molecule inhibitor of USP1 is the compound of Formula III (933). In one embodiment the small molecule inhibitor of USP1 is the compound of Formula IV (527). In one embodiment the small molecule inhibitor of USP1 is the compound of Formula V (947).

Poly(ADP ribose) polymerase (PARP) is a key signaling enzyme involved in triggering repair of single-strand DNA damage. PARP actually includes a family of at least 17 members, including PARP-1 (also known as PARP1 and PARP I) and PARP-2 (also known as PARP2 and PARP II). One important function of PARP-1 is assisting in the repair of single-strand DNA nicks. It binds sites with single strand breaks through its N-terminal zinc fingers and recruits XRCC1, DNA ligase III, DNA polymerase beta and a kinase to the nick, a process called base excision repair (BER). PARP-2 has been shown to oligomerize with PARP1 and therefore is also implicated in BER. The oligomerization has also been shown to stimulate PARP catalytic activity. PARP-1 is also known for its role in transcription through remodeling of chromatin by PARylating histones and relaxing chromatin structure, thus allowing transcription complex to access genes. Several forms of cancer are more dependent on PARP than regular cells, making PARP an attractive target for chemotherapeutic cancer therapy.

Since PARP acts to repair DNA nicks by BER, whereas the FA-BRCA pathway acts to repair DNA defects by a different mechanism, homologous recombination (HR), it is believed that the combined inhibition of the FA-BRCA pathway and of PARP may be significantly more potent than inhibition of either one alone.

As used herein, a "PARP inhibitor" refers to a pharmacological agent that reduces DNA repair by PARP. PARP inhibition has been demonstrated to selectively kill tumor cells lacking components of the homologous recombination (HR) DNA repair pathway while sparing normal cells. Known defects in HR repair include the well-characterized hereditary BRCA1 and BRCA2 mutations in breast and ovarian cancer, as well as nonhereditary BRCA mutations.

Several PARP inhibitors are known in the art and are currently under development, including BSI 201 (BiPar Sciences; 4-iodo-3-nitrobenzamide), olaparib (AZD-2281; Astra Zeneca) (4-[(3-[(4-cyclopropylcarbonyl)piperazin-4-yl]carbonyl)-4-fluorophenyl]methyl(2H)phthalazin-1-one), ABT-888 (veliparib) (2-[(R)-2-methylpyrrolidin-2-yl]-1H-benzimidazole-4-carboxamide), CEP-9722 (Cephalon), MK-4827, KU-0059436 (AZD-2281), LT-673, and 3-aminobenzamide.

In one embodiment a PARP inhibitor is a PARP-1 inhibitor.

In one embodiment the pharmaceutical composition including (a) a small molecule inhibitor of USP1, (b) a PARP inhibitor, and (c) a pharmaceutically acceptable carrier, further includes a DNA cross-linking agent.

It should also be understood that, in addition to compounds of Formula III, Formula IV, and Formula V, and pharmaceutical compositions including said compounds, the invention also embraces structurally related active compounds and pharmaceutical compositions including said structurally related active compounds. Such structurally related active compounds are believed to include compounds according to Formula I, Formula IA, and Formula II, below.

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

One of ordinary skill in the art will appreciate that the synthetic methods, as described herein, utilize a variety of protecting groups. By the term "protecting group," as used herein, it is meant that a particular functional moiety, e.g., O, S, or N, is temporarily blocked so that a reaction can be carried out selectively at another reactive site in a multifunctional compound. In certain embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein. However, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic," as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$— cyclopropyl, vinyl, allyl, n-butyl, sec-butyl, isobutyl, tert-butyl, cyclobutyl, —$CH_2$— cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

The term "amino," as used herein, refers to a primary (—$NH_2$), secondary (—$NHR_x$), tertiary (—$NR_xR_y$), or quaternary (—$N^+R_xR_yR_z$) amine, where $R_x$, $R_y$ and $R_z$ are independently an aliphatic, alicyclic, heteroaliphatic, heterocyclic, aryl, or heteroaryl moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "alkylamino" refers to a group having the structure —NHR', wherein R' is aliphatic, as defined herein. In certain embodiments, the aliphatic group contains 1-20 aliphatic carbon atoms. In certain other embodiments, the aliphatic group contains 1-10 aliphatic carbon atoms. In yet other embodiments, the aliphatic group employed in the invention contain 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "dialkylamino" refers to a group having the structure —NRR', wherein R and R' are each an aliphatic group, as defined herein. R and R' may be the same or different in an dialkyamino moiety. In certain embodiments, the aliphatic groups contains 1-20 aliphatic carbon atoms. In certain other embodiments, the aliphatic groups contains 1-10 aliphatic carbon atoms. In yet other embodiments, the aliphatic groups employed in the invention contain 1-8 aliphatic carbon atoms. In still other embodiments, the aliphatic groups contains 1-6 aliphatic carbon atoms. In yet other embodiments, the aliphatic groups contains 1-4 aliphatic carbon atoms. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

In general, the terms "aryl" and "heteroaryl," as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term "heteroaryl," as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like. In certain embodiments, the term "aryl" or "heteroaryl" refers to a planar ring having p-orbitals perpendicular to the plane of the ring at each ring atom, and satisfying the Huckel rule where the number of pi electrons in the ring is (4n+2) wherein n is an integer.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl) heteroaryl moieties. Thus, as used herein, the phrases "aryl or heteroaryl moieties" and "aryl, heteroaryl, -(alkyl)aryl, -(heteroalkyl)aryl, -(heteroalkyl)heteroaryl, and -(heteroalkyl)heteroaryl" are interchangeable. It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "heteroaliphatic," as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments described herein.

The terms "halo" and "halogen" as used herein refer to an atom selected from fluorine, chlorine, bromine, and iodine.

In certain embodiments, the compound of the invention or for use in the invention is of the formula:

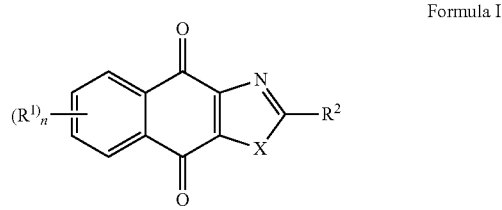

Formula I wherein

X is O, S, or NR$^3$;

n is 0, 1, 2, 3, or 4;

each occurrence of R$^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^A$; —C(=O)R$^A$; —C(=O)N(R$^A$)$_2$; —CO$_2$R$^A$; —CN; —SCN; —SR$^A$; —SOR$^A$; —SO$_2$R$^A$; —NO$_2$; —N$_3$; —N(R$^A$)$_2$; —NHC(=O)R$^A$; —NR$^A$C(=O)N(R$_A$)$_2$; —OC(=O)OR$^A$; —OC(=O)R$^A$; —OC(=O)N(R$^A$)$_2$; —NR$^A$C(=O)OR$^A$; or —C(R$^A$)$_3$; wherein each occurrence of R$^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^B$; —C(=O)R$^B$; —C(=O)N(R$^B$)$_2$; —CO$_2$R$^B$; —CN; —SCN; —SR$^B$; —SOR$^B$; —SO$_2$R$^B$; —NO$_2$; —N$_3$; —N(R$^B$)$_2$; —NHC(=O)R$^B$; —NR$^B$C(=O)N(R$^B$)$_2$; —OC(=O)OR$^B$; —OC(=O)R$^B$; —OC(=O)N(R$^B$)$_2$; —NR$^B$C(=O)OR$^B$; or —C(R$^B$)$_3$; wherein each occurrence of R$^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$^3$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and pharmaceutically acceptable salts thereof.

In one embodiment, a compound of Formula I is the compound of Formula IV (527):

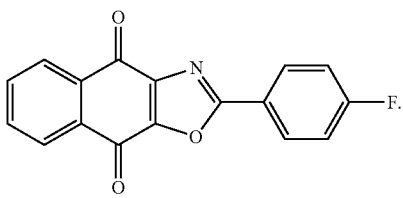 [SMILES: O=C1c2ccccc2C(=O)c2oc(-c3ccc(F)cc3)nc21]

Certain embodiments of Formula I are disclosed in WO 97/21684 and WO 97/21710, the entire contents of both of which are hereby incorporated by reference. WO 97/21684 and WO 97/21710 disclose compounds in accordance with Formula I are useful for treating diseases related to venous insufficiency and inflammatory edema.

In certain embodiments, a compound of Formula I is any one of the following compounds: 1,2-dimethyl-1H-naphth[2,3-d]imidazole-4,9-dione (Registry No. 4572-59-2, Ryan Scientific, Inc., Mt. Pleasant, S.C.); 1,2,3,4-tetrahydro-naphth[2',3':4,5]imidazo[1,2-1]pyrazine-6,11-dione (Registry No. 132545-27-8, Ryan Scientific, Inc.); 2-(pentafluorophenyl)-1H-naphtho[2,3-d]imidazole-4,9-dione (Registry No. 418805-36-4, ChemBridge Corp., San Diego, Calif.); 2-(4-fluorophenyl)-1-(4-methylphenyl)-1H-naphth[2,3-d]imidazole-4,9-dione (Registry No. 325731-50-8, Ryan Scientific, Inc.); and 1-phenyl-1H-naphth[2,3-d]imidazole-4,9-dione (Registry No. 15030-17-8, TimTec, Inc., Newark, Del.).

In certain embodiments, the compound is in a reduced form of the formula:

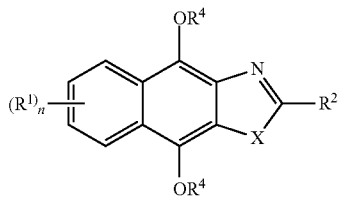

Formula IA wherein n, $R^1$, $R^2$, and X are defined as above; and each occurrence of $R^4$ is independently hydrogen, an oxygen protecting group, cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —C(=O)$R^D$; —CO$_2$$R^D$; —C(=O)N($R^D$)$_2$; or —C($R^D$)$_3$; wherein each occurrence of $R^D$ is independently a hydrogen, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and pharmaceutically acceptable salts thereof.

In certain embodiments, X is O. In certain embodiments, X is S. In certain embodiments, X is NH. In certain embodiments, X is $NR^3$.

In certain embodiments, n is 0. In certain embodiments, n is 1. In certain embodiments, n is 2. In certain embodiments, n is 3. In certain embodiments, n is 4.

In certain embodiments, at least one $R^1$ is halogen. In certain embodiments, at least one $R^1$ is $C_{1-6}$ alkyl. In certain embodiments, at least one $R^1$ is —$OR^A$. In certain embodiments, at least one $R^1$ is —$N(R^A)_2$. In certain embodiments, at least one $R^1$ is —$NO_2$. In certain embodiments, at least one $R^1$ is —CN. In certain embodiments, at least one $R^1$ is —SCN.

In certain embodiments, $R^2$ is substituted or unsubstituted aryl. In certain embodiments, $R^2$ is unsubstituted aryl. In certain embodiments, $R^2$ is substituted aryl. In certain embodiments, $R^2$ is substituted or unsubstituted phenyl. In certain embodiments, $R^2$ is unsubstituted phenyl. In certain embodiments, $R^2$ is substituted phenyl. In certain embodiments, $R^2$ is ortho-substituted phenyl. In certain embodiments, $R^2$ is meta-substituted phenyl. In certain embodiments, $R^2$ is para-substituted phenyl. In certain embodiments, $R^2$ is phenyl substituted with a halogen. In certain embodiments, $R^2$ is substituted or unsubstituted heteroaryl. In certain embodiments, $R^2$ is unsubstituted heteroaryl. In certain embodiments, $R^2$ is substituted heteroaryl. In certain embodiments, $R^2$ is 5-membered, substituted or unsubstituted heteroaryl. In certain embodiments, $R^2$ is 6-membered, substituted or unsubstituted heteroaryl.

In certain embodiments, the compound of the invention or for use in the invention is of the formula:

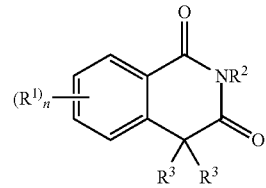

Formula II wherein n is 0, 1, 2, 3, or 4;

each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^A$; —C(=O)$R^A$; —CO$_2R^A$; —C(=O)N($R^A$)$_2$; —CN; —SCN; —$SR^A$; —$SOR^A$; —SO$_2R^A$; —NO$_2$; —N$_3$; —N($R^A$)$_2$; —NHC(=O)$R^A$; —$NR^A$C(=O)N($R_A$)$_2$; —OC(=O)$OR^A$; —OC(=O)$R^A$; —OC(=O)N($R^A$)$_2$; —$NR^A$C(=O)$OR^A$; or —C($R^A$)$_3$; wherein each occurrence of $R^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^2$ is hydrogen; a nitrogen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —C(=O)$R^B$; —C(=O)N($R^B$)$_2$; —CO$_2R^B$; or —C($R^B$)$_3$; wherein each occurrence of $R^B$ is independently a hydrogen, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

each occurrence of $R^3$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^C$; —$C(=O)R^C$; —$C(=O)N(R^C)_2$; —$CO_2R^C$; —CN; —SCN; —$SR^C$; —$SOR^C$; —$SO_2R^C$; —$NO_2$; —$N_3$; —$N(R^C)_2$; —$NHC(=O)R^C$; —$NR^CC(=O)N(R^C)_2$; —$OC(=O)OR^C$; —$OC(=O)R^C$; —$OC(=O)N(R^C)_2$; —$NR^CC(=O)OR^C$; or —$C(R^C)_3$; wherein each occurrence of $R^C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; wherein both occurrences of $R^3$ may optionally be taken together with the intervening carbon atoms to form an optionally substituted cyclic moiety or may be =O, =S, or =$NR^C$; and pharmaceutically acceptable salts thereof.

In certain embodiments, n is 0. In certain embodiments, n is 1. In certain embodiments, n is 2. In certain embodiments, n is 3. In certain embodiments, n is 4.

In certain embodiments, at least one $R^1$ is halogen. In certain embodiments, at least one $R^1$ is $C_{1-6}$ alkyl. In certain embodiments, at least one $R^1$ is —$OR^A$. In certain embodiments, at least one $R^1$ is —$N(R^A)_2$. In certain embodiments, at least one $R^1$ is —$NO_2$. In certain embodiments, at least one $R^1$ is —CN. In certain embodiments, at least one $R^1$ is —SCN.

In certain embodiments, $R^2$ is hydrogen. In certain embodiments, $R^2$ is substituted or unsubstituted, branched or unbranched acyl. In certain embodiments, $R^2$ is cyclic or acyclic, substituted or unsubstituted, branched or unbranched aliphatic. In certain embodiments, $R^2$ is cyclic or acyclic, substituted or unsubstituted, branched or unbranched heteroaliphatic. In certain embodiments, $R^2$ is substituted or unsubstituted aryl. In certain embodiments, $R^2$ is substituted or unsubstituted heteroaryl. In certain embodiments, $R^2$ is optionally substituted heteroarylalkyl. In certain embodiments, $R^2$ is optionally substituted arylalkyl. In certain embodiments, $R^2$ is —$CH_2$-heteroaryl. In certain embodiments, $R^2$ is of the formula:

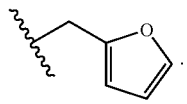 [SMILES: *Cc1ccco1]

In certain embodiments, $R^2$ is of the formula:

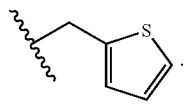 [SMILES: *Cc1ccc[nH]1]

In certain embodiments, $R^2$ is of the formula:

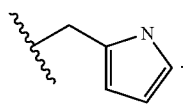

In certain embodiments, $R^2$ is —$CH_2$-aryl.

In certain embodiments, both $R^3$ are hydrogen. In certain embodiments, at least one $R^3$ is halogen. In certain embodiments, at least one $R^3$ is fluorine. In certain embodiments, at least one $R^3$ is $C_{1-6}$ alkyl. In certain embodiments, at least one $R^3$ is —$OR^C$. In certain embodiments, at least one $R^3$ is —$N(R^C)_2$.

In one embodiment, a compound of Formula II is the compound of Formula V (947):

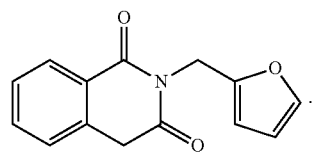 [SMILES: O=C1Cc2ccccc2C(=O)N1Cc1ccco1]

As noted above, a method for synthesizing the compound of Formula V (947) is disclosed in Sondhi et al. (2008) *Letts Org Chem* 5:51-4, but this reference does not disclose a use for this compound.

In certain embodiments, a compound of Formula II is any one of the following compounds: 2-(2-furanylmethyl)-7-methoxy-1,3(2H,4H)-isoquinolinedione (Registry No. 328039-10-7, Ryan Scientific, Inc.); 2-benzyl-1,3(2H,4H)-isoquinolinedione (Registry No. 21640-31-3, Key Organics Ltd., Camelford, United Kingdom); 2-(4-methoxybenzyl)-1,3(2H,4H)-isoquinolinedione (Registry No. 217493-71-5, Key Organics, Ltd.); 2-(2-phenylethyl)-1,3(2H,4H)-isoquinolinedione (Registry No. 53558-67-1, ChemBridge Corp.); 3-(2-furanylmethyl)-2,4,(1H,3H)-quinazolinedione (Registry No. 436855-78-6, Ryan Scientific, Inc.); 3-(2-furanylmethyl)-1-methyl-2,4,(1H,3H)-quinazolinedione (Registry No. 531504-02-6, Enamine, Kiev, Ukraine); 2-(2-furylmethyl)-1H-isoindole-1,3(2H)-dione (Registry No. 4667-83-8, ChemBridge Corp.); 2-(2-(3,4-dimethoxyphenyl)ethyl)isoquinoline-1,3(2H,4H)-dione (Registry No. 198139-89-8, Sigma-Aldrich, St. Louis, Mo.); and 2-benzo[1,3]dioxol-5-ylmethyl-4H-isoquinoline-1,3-dione (Registry No. 565193-20-6, Ryan Scientific, Inc.).

It should be understood that, in addition to compounds of Formula III (933), Formula IV (527), and Formula V (947), and likewise related compounds as disclosed above, and pharmaceutical compositions including said compounds, the invention also embraces pharmaceutically acceptable salts of said compounds and pharmaceutical compositions including said pharmaceutically acceptable salts of said compounds. As used herein, a "pharmaceutically acceptable salt" refers to an acid or base form of a compound, usually in combination with a counter ion, that is suitable for use in pharmacy. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group. Pharmaceutically acceptable salts are well known in the art and are the subject of numerous reviews and monographs such as P. H. Stahl and C. G. Wermuth, editors, *Handbook of Pharmaceutical Salts: Properties, Selection and Use*, Weinheim/Zürich:Wiley-VCH/VHCA, 2002.

The invention further provides pharmaceutical compositions of the invention formulated for targeted delivery to a cancer cell. As used herein, a "cancer cell" refers to a living cell in or isolated from a cancer. "Cancer" as used herein refers to an uncontrolled growth of cells. Cancers which migrate from their original location and seed vital organs can eventually lead to the death of the subject through the functional deterioration of the affected organs. Cancers include, but are not limited to, basal cell carcinoma, biliary tract cancer; bladder cancer; bone cancer; brain and CNS cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia; liver cancer; lung cancer (e.g. small cell and non-small cell); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas.

Certain cancer cells express cancer antigens on their cell surface, thereby making it possible to target delivery of an agent to the cancer cells. A "cancer antigen" as used herein is a compound, such as a peptide or protein, associated with a tumor or cancer cell surface and which is capable of provoking an immune response when expressed on the surface of an antigen presenting cell in the context of an MHC molecule. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses. Cancer antigens can be prepared from cancer cells either by preparing crude extracts of cancer cells, for example, as described in Cohen, et al., 1994, *Cancer Research*, 54:1055, by partially purifying the antigens, by recombinant technology, or by de novo synthesis of known antigens. Cancer antigens include but are not limited to antigens that are recombinantly expressed, an immunogenic portion of, or a whole tumor or cancer. Such antigens can be isolated or prepared recombinantly or by any other means known in the art.

A pharmaceutical composition formulated for targeted delivery to a cancer cell includes a delivery vehicle that contains or is coated with an active agent, such as a small molecule USP1 inhibitor of the invention, linked to a targeting agent that is specific for a cancer antigen or other target molecule of interest that is present on the cancer cell. A delivery vehicle can be a nanosphere, microsphere, emulsome, liposome, or virosome, any of which can be prepared using methods well known in the art. A targeting agent can be an antigen-specific antibody or antigen-binding fragment thereof, a receptor, or counter-receptor. As an example, a receptor-counter-receptor pair can be a growth factor receptor and the corresponding growth factor that binds to the growth factor receptor. In one embodiment, the targeting agent can include biotin or a biotinylated molecule that binds to avidin or streptavidin that is present on the surface of a cancer cell. In one embodiment, the targeting agent can include avidin or streptavidin that binds to biotin or a biotinylated molecule that is present on the surface of a cancer cell.

The invention provides a method for inhibiting USP1-mediated deubiqitination of a ubiquitinated substrate, whereby the ubiquitinated substrate is contacted with a small molecule inhibitor of USP1 selected from the group consisting of a compound of Formula I, a compound of Formula IA, a compound of Formula II, the compound of Formula III (933), the compound of Formula IV (527), the compound of Formula V (947), and any combination thereof, in an amount effective to inhibit USP1-mediated deubiqitination of the ubiquitinated substrate. In one embodiment the small molecule inhibitor of USP1 is the compound of Formula III (933). In one embodiment the small molecule inhibitor of USP1 is the compound of Formula IV (527). In one embodiment the small molecule inhibitor of USP1 is the compound of Formula V (947). The method can be performed in vitro or in vivo. In one embodiment the ubiquitinated substrate is an isolated ubiquitinated substrate. A substrate or other compound is "isolated" when it is substantially separated from other cellular components with which it is found in nature. In one embodiment an isolated substrate is a substrate that has been purified from a natural source. In one embodiment the isolated substrate is expressed artificially by a host cell and then separated from the host cell.

In one embodiment the substrate is a natural substrate of USP1. For example, in one embodiment the substrate is ubiquitinated FANCD2 (FANCD2-Ub). In one embodiment the substrate is ubiquitinated PCNA (PCNA-Ub).

In one embodiment the substrate is an artificial substrate of USP1. For example, in one embodiment the substrate is ubiquitinated AMC (AMC-Ub).

The invention provides a method for treating a subject having cancer, whereby a small molecule inhibitor of USP1 selected from the group selected from the group consisting of a compound of Formula I, a compound of Formula IA, a compound of Formula II, the compound of Formula III (933), the compound of Formula IV (527), the compound of Formula V (947), and any combination thereof, is administered to a subject having cancer in need of such treatment in an amount effective to treat the cancer. In one embodiment the small molecule inhibitor of USP1 is the compound of Formula III (933). In one embodiment the small molecule inhibitor of USP1 is the compound of Formula IV (527). In one embodiment the small molecule inhibitor of USP1 is the compound of Formula V (947).

As used herein, a "subject having a cancer" refers to a living mammal with a detectable cancer. In one embodiment the subject is a human. Methods for detecting cancer are well known in the art. Such methods include biopsy, blood smear, bone marrow biopsy, X-ray, CAT scan, magnetic resonance imaging (MRI), radionuclide scanning, polymerase chain reaction (PCR), and the like.

The compound can be administered to the subject using any suitable route of administration. Such routes of administration can include oral, intravenous, intramuscular, intraperitoneal, intravesical, intracisternal, other direct injection (e.g., into a tumor), topical, aerosol to lung, rectal, vaginal, and other mucosal.

As used herein, an "effective amount" is an amount that is sufficient to realize a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is effective to treat the particular subject. The effective amount for any particular application can vary depending on such factors as the disease or condition being treated, the particular active agent being administered, the size of the subject, or the severity of the disease or condition. One of ordinary skill in the art can empirically determine the effective amount of a particular active agent and/or other therapeutic agent without necessitating undue experimentation. It is preferred generally that a maximum dose be used, that is, the highest safe dose according to sound medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

For any compound described herein the therapeutically effective amount can be initially determined from animal models. A therapeutically effective dose can also be determined from human data for active agents which have been tested in humans and for compounds which are known to exhibit similar pharmacological activities, such as other related active agents. Higher doses may be required for enteral administration as compared to parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

Generally, daily oral doses of active compounds will be from about 0.01 milligrams/kg per day to 1000 milligrams/kg per day. It is expected that oral doses in the range of 0.5 to 50 milligrams/kg, in one or several administrations per day, will yield the desired results. Dosage may be adjusted appropriately to achieve desired drug levels, local or systemic, depending upon the mode of administration. For example, it is expected that intravenous administration would be from an order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

As used herein, the term "treat" means to reduce or ameliorate a disease or condition by a detectable amount or degree. The term "treat" as used herein refers to both complete and partial treatment. In the context of cancer, the term "treat" as used herein thus can refer to complete or partial remission of a cancer. For example, treating a tumor may be manifest as a halted or slowed progression in the size or volume of a tumor, a decrease in the size or volume of a tumor, or complete resolution of a tumor.

The method can be combined with at least one additional cancer treatment agent. For example, in one embodiment the method further includes administering to the subject a DNA cross-linking agent. In one embodiment the method further includes administering to the subject a PARP inhibitor. In one embodiment the method further includes administering to the subject a DNA cross-linking agent and a PARP inhibitor. The additional cancer treatment agent can be administered either essentially simultaneously or sequentially with respect to the administering of the small molecule USP1 inhibitor. When the administering is sequential, either agent can be administered before the other. Alternatively or in addition, the administering of the small molecule USP1 inhibitor and the administering of the at least one additional cancer treatment agent can be at least partially overlapping in time or non-overlapping in time. Furthermore, the administering of the small molecule USP1 inhibitor and the administering of the at least one additional cancer treatment agent can be accomplished using the same or different routes of administration, as may be appropriate.

It is believed that cancers that do not express USP1 are particularly sensitive to DNA cross-linking agents. It is also believed that cancers that do not express UAF1 are particularly sensitive to DNA cross-linking agents. Conversely, it is believed that cancers that do express USP1 are resistant to DNA cross-linking agents. It is also believed that cancers that do express USP 1 and UAF1 are particularly resistant to DNA cross-linking agents. A cancer that does express USP1 can therefore be sensitized to DNA cross-linking agents by contacting the cancer with a USP1 inhibitor.

The invention provides a method for sensitizing a cancer to a DNA cross-linking agent, whereby a cancer is contacted with a small molecule inhibitor of USP1 selected from the group selected from the group consisting of a compound of Formula I, a compound of Formula IA, a compound of Formula II, the compound of Formula III (933), the compound of Formula IV (527), the compound of Formula V (947), and any combination thereof, in an amount effective to sensitize the cancer to a DNA cross-linking agent. In one embodiment the small molecule inhibitor of USP1 is the compound of Formula III (933). In one embodiment the small molecule inhibitor of USP1 is the compound of Formula IV (527). In one embodiment the small molecule inhibitor of USP1 is the compound of Formula V (947). The method can be performed in vitro or in vivo. In one embodiment the cancer expresses USP1. In one embodiment the cancer expresses both USP1 and UAF1.

As used herein, to "sensitize" means to make more susceptible. A cancer or cancer cell is sensitized to a DNA cross-linking agent according to the method when it is made more susceptible to the DNA cross-linking agent than it was, or otherwise would have been, without the contacting with the small molecule USP1 inhibitor.

In one embodiment the DNA cross-linking agent is a chemotherapy agent selected from the group consisting of cisplatin, carboplatin, oxaliplatin, alkylating agents, mitomycin C, and any combination thereof. In one embodiment the DNA cross-linking agent is cisplatin.

In one embodiment the DNA cross-linking agent is ionizing radiation, for example, X-ray therapy, cobalt-60 gamma ray irradiation, cesium-137 gamma ray irradiation, iridium-192 gamma ray irradiation, other external beam radiotherapy, and brachytherapy.

The invention provides a method to identify a cancer that is responsive to USP1 inhibition, whereby cancer cells from a cancer are contacted with a small molecule inhibitor of USP1 selected from the group consisting of a compound of Formula I, a compound of Formula IA, a compound of Formula II, the compound of Formula III (933), the compound of Formula IV (527), the compound of Formula V (947), and any combination thereof; and measuring USP1 activity in the cancer cells contacted with the small molecule inhibitor of USP1, wherein reduced USP1 activity in the cancer cells contacted with the small molecule inhibitor of USP1 relative to control USP1 activity in the cancer cells not contacted with the small molecule inhibitor of USP1 identifies the cancer as a cancer that that is responsive to USP1 inhibition. In one embodiment the small molecule inhibitor of USP1 is the compound of Formula III (933). In one embodiment the small molecule inhibitor of USP1 is the compound of Formula IV (527). In one embodiment the small molecule inhibitor of USP1 is the compound of Formula V (947). The method can be performed in vitro or in vivo. Alternatively or in addition, individual steps of the method can be performed, independent of each other, in vitro or in vivo. In vitro methods and, likewise, in vitro method steps, can be performed in a cell-free assay or in a cell-based assay.

The term "cancer cells from a cancer" as used herein can refer to cancer cells isolated from a cancer or to cancer cells in situ in a cancer.

In one embodiment the method is a method to identify a subject having a cancer that is responsive to USP1 inhibition, whereby cancer cells from a subject having a cancer are contacted with a small molecule inhibitor of USP1 selected from the group consisting of a compound of Formula I, a compound of Formula IA, a compound of Formula II, the compound of Formula III (933), the compound of Formula IV (527), the compound of Formula V (947), and any combination thereof; and measuring USP1 activity in the cancer cells contacted with the small molecule inhibitor of USP1, wherein reduced USP1 activity in the cancer cells contacted with the small molecule inhibitor of USP1 relative to control USP1 activity in the cancer cells not contacted with the small molecule inhibitor of USP1 identifies the subject as a subject having a cancer that that is responsive to USP1 inhibition.

The term "cancer cells from a subject having a cancer" as used herein can refer to cancer cells isolated from a subject having a cancer or to cancer cells in situ in subject having a cancer.

USP1 activity can be measured by any of the assays described herein. For example, activity can be measured by measuring the level of deubiquitinated target protein in response to USP1/UAF1 (that is, for example, the conversion of AMC-Ub to AMC). In one embodiment, an assay to measure USP1 deubiquitination activity includes the steps of contacting a preparation comprising USP1 (and optionally UAF1) with a ubiquitinated target, e.g., AMC-Ub, and measuring fluorescence emission. Cleavage of ubiquitin from AMC-Ub releases the fluorogenic AMC moiety, which can be detected as an increase in fluorescence emission at 460 nm ($\lambda_{ex}$=380 nm). Dang et al. (1998) *Biochemistry* 37:1868-79.

For measurement of USP1 activity in a cell-based assay, levels of ubiquitinated FANCD2-Ub and unubiquitinated FANCD2, or levels of ubiquitinated PCNA-Ub and unubiquitinated PCNA can be measured, for example by immunoblotting whole cell lysates with anti-FANCD2 antibody (e.g., sc-20022; Santa Cruz Biotechnology, Inc.) or anti-PCNA antibody (e.g., sc-56; Santa Cruz Biotechnology, Inc.), respectively.

Assays to determine the deubiquitinase activity of USP1 can be performed in a cell-based assay, for example, in which USP1 (and optionally UAF1) are recombinantly expressed in a cell (such as *E. coli* or SF9 insect cells) along with the target, or in a cell-free assay in which, for example, USP1 (or a USP1/UAF1 complex) is contacted in vitro with a candidate inhibitor in the presence of a ubiquitinated target.

The invention provides a method to identify a cancer that is responsive to combined DNA cross-linking therapy and USP1 inhibition, whereby cancer cells from a cancer are contacted with a DNA cross-linking agent and a small molecule inhibitor of USP1 selected from the group consisting of a compound of Formula I, a compound of Formula IA, a compound of Formula II, the compound of Formula III (933), the compound of Formula IV (527), the compound of Formula V (947), and any combination thereof; and proliferation of the cancer cells contacted with the DNA cross-linking agent and the small molecule inhibitor of USP1 is measured, wherein reduced proliferation of the cancer cells contacted with the DNA cross-linking agent and the small molecule inhibitor of USP1 relative to control proliferation of the cancer cells contacted with the DNA cross-linking agent but not the small molecule USP1 inhibitor identifies the cancer as a cancer that is responsive to DNA cross-linking therapy together with USP1 inhibition. In one embodiment the small molecule inhibitor of USP1 is the compound of Formula III (933). In one embodiment the small molecule inhibitor of USP1 is the compound of Formula IV (527). In one embodiment the small molecule inhibitor of USP1 is the compound of Formula V (947). The method can be performed in vitro or in vivo. Alternatively or in addition, individual steps of the method can be performed, independent of each other, in vitro or in vivo. In vitro methods and, likewise, in vitro method steps, can be performed in a cell-free assay or in a cell-based assay.

In one embodiment the method is a method to identify a subject having a cancer that is responsive to combined DNA cross-linking therapy and USP1 inhibition, whereby cancer cells from a subject having a cancer are contacted with a DNA cross-linking agent and a small molecule inhibitor of USP1 selected from group consisting of a compound of Formula I, a compound of Formula IA, a compound of Formula II, the compound of Formula III (933), the compound of Formula IV (527), the compound of Formula V (947), and any combination thereof; and proliferation of the cancer cells contacted with the DNA cross-linking agent and the small molecule inhibitor of USP1 is measured, wherein reduced proliferation of the cancer cells contacted with the DNA cross-linking agent and the small molecule inhibitor of USP1 relative to control proliferation of the cancer cells contacted with the DNA cross-linking agent but not the small molecule USP1 inhibitor identifies the subject as a subject having a cancer that is responsive to DNA cross-linking therapy together with USP1 inhibition.

The term "combined DNA cross-linking therapy and USP1 inhibition" as used herein refers to any combination of DNA cross-linking therapy and USP1 inhibition. "DNA cross-linking therapy" refers to the administration to a subject of at least one DNA cross-linking agent, as defined herein. "USP1 inhibition" refers to the administration to a subject of at least one small molecule USP1 inhibitor. In one embodiment a small molecule USP1 inhibitor is a small molecule USP1 inhibitor of the invention. The administration of the DNA cross-linking agent and the USP1 inhibitor can be accomplished either essentially simultaneously or sequentially with respect to the administering of the USP1 inhibitor. When the administering is sequential, either agent can be administered before the other. Alternatively or in addition, the administering of the small molecule USP1 inhibitor and the administering of the at least one DNA cross-linking agent can be at least partially overlapping in time or non-overlapping in time. Furthermore, the administering of the small molecule USP1 inhibitor and the administering of the at least one DNA cross-linking agent can be accomplished using the same or different routes of administration, as may be appropriate.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the active agent can be administered to a subject by any mode that delivers the active agent to the desired surface. Administering the pharmaceutical composition of the present invention may be accomplished by any means known to the skilled artisan. Preferred routes of administration include but are not limited to oral, parenteral, intramuscular, intranasal, sublingual, intratracheal, inhalation, ocular, vaginal, and rectal.

For oral administration, the compounds (e.g., compounds of Formula III-V, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the active agent (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the active agent (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the active agent or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the active agents (or derivatives thereof). The active agent (or derivative) is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13 (suppl. 5):143-146 (endothelin-1); Hubbard et al., 1989, Annals of Internal Medicine, Vol. III, pp. 206-212 (al-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of active agent (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified active agent may also be prepared in different formulations depending on the type of chemical modification or the type of device employed.

Formulations suitable for use with a nebulizer, either jet or ultrasonic, will typically comprise active agent (or derivative) dissolved in water at a concentration of about 0.1 to 25 mg of biologically active active agent per mL of solution. The formulation may also include a buffer and a simple sugar (e.g., for active agent stabilization and regulation of osmotic pressure). The nebulizer formulation may also contain a surfactant, to reduce or prevent surface induced aggregation of the active agent caused by atomization of the solution in forming the aerosol.

Formulations for use with a metered-dose inhaler device will generally comprise a finely divided powder containing the active agent (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing active agent (or derivative) and may also include a bulking agent, such as lactose, sorbitol, sucrose, or mannitol in amounts which facilitate dispersal of the powder from the device, e.g., 50 to 90% by weight of the formulation. The active agent (or derivative) should most advantageously be prepared in particulate form with an average particle size of less than 10 micrometers (m), most preferably 0.5 to 5 µm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The active agents and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The therapeutic agent(s), including specifically but not limited to the active agent, may be provided in particles. Particles as used herein means nano or microparticles (or in some instances larger) which can consist in whole or in part of the active agent or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the active agent in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in *Macromolecules*, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

The present invention is further illustrated by the following Examples, which in no way should be construed as further limiting. The entire contents of all of the references (including literature references, issued patents, published patent applications, and co-pending patent applications, if any) cited throughout this application are hereby expressly incorporated by reference.

EXAMPLES

Materials and Methods
Cell Lines, Enzymes and Compounds

HeLa and U2OS-DRGFP cells were grown in Dulbecco's modified Eagle's medium (Invitrogen) supplemented with 15% fetal bovine serum (Invitrogen) and penicillin/streptomycin glutamine (Invitrogen). Purified USP5 enzyme was purchased from Boston Biochem. UCH-L1 and UCL-H3 were as reported previously (Mermerian et al, *Bioorganic & Medicinal Chemistry Letters*, 17:3729). C526 was synthesized and the purity validated by high-performance liquid chromatography.
Purification of USP1 and UAF1 Protein Complex The co-purification of USP1/UAF1 complex was performed as described previously (Cohn et al, Mol Cell, 2007). N-terminal His-tagged USP1 GG670/671AA was expressed using pFASTBac-HTa vector (Invitrogen), and UAF1 were expressed using pFASTBac-1 vector (Invitrogen). Each recombinant virus was produced by transfecting the corresponding bacmid to Sf9 cells. For the purification, cell pellets were re-suspended in lysis buffer (50 mM Tris-HCl [pH 8.0], 150 mM NaCl, 10 mM BME, 10 mM imidazole, 10% glycerol, and 0.2% Triton X-100) and sonicated to lyse. Lysates were centrifuged, and the supernatants were incubated with Ni-NTA agarose resin (QIAGEN) for 1 hr. The resin was washed extensively, and the proteins were eluted in elution buffer (50 mM Tris-HCl [pH 8.0], 100 mM NaCl, 10 mM BME, 10% glycerol, and 250 mM imidazole). Eluted protein was bound to a 5 ml HiTrap Q-FF cartridge (GE Biosciences), washed with washing buffer (50 mM Tris-HCl [pH 8.0], 100 mM KCl, 5 mM DTT, 0.1 mM EDTA, and 10% glycerol), eluted in the same buffer containing 500 mM KCl and stocked at −80° C. After final purification, the protein concentration was measured using Bradford assay and the quality of the protein was determined by SDS-PAGE and coomassie blue staining.
In Vitro Deubiquitination Assay The in vitro enzymatic assays were performed using purified proteins from Sf9 cells as described previously (Cohn et al.). The assays using ubiquitin-AMC (Ub-7-amido-4-methylcoumarin; Boston Biochem) as substrate was carried out in a reaction buffer containing 20 mM HEPES-KOH (pH 7.8), 20 mM NaCl, 0.1 mg/ml ovalbumin, 0.5 mM EDTA and 10 mM dithiothreitol. The fluorescence was measured by FluoStar Galaxy Fluorometer (BMG Labtech). For the Ub-vinylsulfone (VS) assay, the proteins were incubated with Ub-VS at 0.5 µM final concentration for 1 h at 30° C., followed by the immunoblotting analysis.
High Throughput Screening The ubiquitin-Rho based enzyme assay for high throughput screening was established in a 384-well format. The reaction buffer containing and USP1/UAF1 complex were added in 384 well plates using automated liquid handling robot-Bio-Tek Microfill (Bio-Tek Instrments Inc., VT), followed by addition of the compounds (in DMSO) from the compound library plates to wells using a pin transfer robotic system at a final concentration of 10 µM. The reaction was composed of 0.1 nM purified USP1/UAF complex, 75 nM ubiquitin Rhodamine (Ub-Rho, Boston Biochem, U-600) and 2 µM ubiquitin. Fluorescence was monitored in a FluoStar Galaxy Fluorometer (BMG Labtech). Fluorescence emission at 535 nm ($\lambda ex$=485 nm) was measured in an automated plate reader Envision 2 (Perkin Elmer, Mass.).
Clonogenic Assay Cells were seeded in 6-well plate at 500 cells per well followed by treatment with C527. Colonies were allowed to grow for 7-10 days, fixed with a solution containing 10% Methanol and 10% acetic acid at room temperature for 15 min and then stained with 1% crystal violet in methanol. Colonies of >50 cells were counted, and the surviving fraction was calculated and normalized to untreated control.
HR Analysis HR repair activity was analyzed using DR-GFP reporter as previously described (Pierce A J et al, Genes Dev, 13: 2633). U2OS-DRGFP cells carrying a chromosomally integrated single copy of HR repair substrate were used to test the effect of C527 on HR. DSB-induced HR results in restoration and expression of GFP and was quantified by FACS. Briefly, 24 h after induction of chromosomal double-strand breaks through the expression of I-SceI, cells were treated with C527 for 24 h. Cells were subjected to FACS analysis and the percentage of GFP-positive cells was quantitated relative to the total viable cell number. For each analysis, 100,000 cells were processed.
Immunofluorescence Cells were pre-extracted with extraction buffer (0.25% Triton-X100 in 200 mM HEPES at pH 7.4, 50 mM NaCl, 3 mM $MgCl_2$ and 300 mM sucrose) on ice for 2 min prior to fixation with 4% paraformaldehyde. RAD51 foci were detected using anti-RAD51 antibody (Santa Cruz Biotechnology) and visualized using Alexa Fluor 488-conjugated secondary antibody. The quantification of cells with RAD51 foci was performed by counting the number of cells with RAD51 foci. At least 200 cells were counted from each sample. Data are represented as mean±SD from three independent experiments.

MTT Assay

HeLa cells were seeded in 96-well plate and treated with C527 for 4 more days. 20 µL MTT (Sigma) at 5 mg/mL was added to each well and cells were left at 37° C. for incubation. 4 h later, the metabolic product was dissolved in a solution containing 10% SDS, 5% isopropanol and 0.01 mol/L HCl. Optical density at 565 nm was measured in an automated plate reader. The percentage of cell survival was determined by normalizing to solvent vehicle treated cells.

Example 1. Recombinant USP1

Recombinant USP1 protein purified from Sf9 cells was expressed using pFastBac-HTa vector (Invitrogen) containing an N-terminal His tag. For USP1 and USP1/UAF1 complex purification, cell pellets were resuspended in lysis buffer (50 mM Tris-HCl, pH 8.0, 150 mM NaCl, 10 mM β-mercaptoethanol, 10 mM imidazole, 10% glycerol and 0.2% Triton X-100) and sonicated to lyse. Lysates were centrifuged and the supernatants were incubated with Ni-NTA agarose resin (Qiagen) for 1 hour. The resin was washed extensively and the proteins eluted in elution buffer (50 mM Tris-HCl, pH 8.0, 100 mM NaCl, 10 mM β-mercaptoethanol, 10% glycerol and 250 mM imidazole). Eluted protein was bound to a 5 mL HiTrap Q-FF cartridge (GE Biosciences), washed with washing buffer (50 mM Tris-HCl, pH 8.0, 100 mM KCl, 5 mM DTT, 0.1 mM EDTA and 10% glycerol) and eluted in the same buffer containing 500 mM KCl.

Example 2. Recombinant UAF1

Recombinant UAF1 protein purified from Sf9 cells was expressed using pFastBac-1 vector (Invitrogen) with an engineered C-terminal Strep II tag. Cell pellets were resuspended in lysis buffer (50 mM Tris-HCl, pH 8.0, 150 mM NaCl, 2 mM DTT, 10% glycerol), centrifuged, and the clarified lysate was incubated for 1 hour with the Strep-Tactin resin (Novagen). Following incubation, the resin was washed extensively and the protein eluted in the same buffer containing 2.5 mM desthiobiotin.

Example 3. Purification of Native USP1/UAF1 Complex

USP1 enzyme was purified with associated proteins as a native protein complex from HeLa cells. A HeLa cell line stably expressing a Flag- and HA-epitope tagged fusion protein of USP1 (e-USP1) was generated by retroviral transduction. The exogenous e-USP1 protein was expressed at levels comparable to the endogenous protein and also underwent autocleavage, a feature previously reported for the USP1 protein. Huang et al. (2006) *Nat Cell Biol* 8:339-47; Nijman et al. (2005) *Mol Cell* 17:331-9.

Nuclear extract was prepared from HeLa cells, and the native USP1 complex was purified by a two-step immuno-affinity purification scheme. Nakatani and Ogryzko (2003) *Methods Enzymol* 370:430-44. SDS-PAGE analysis of the purified complex demonstrated the presence of multiple polypeptides. No polypeptides were observed in a mock purification from untransduced HeLa cells, indicating that all polypeptides copurifying with e-USP1 were bona fide subunits of the USP1 complex. Mass spectrometric analysis of the polypeptides identified full length USP1, the N-terminal cleavage product of USP1, and the C-terminal cleavage product of USP1. A fourth major polypeptide, with a molecular weight of 80 kDa, was identified as the previously studied p80 protein. Park et al. (2002) *Immunity* 17:221-33. This protein is now referred to as UAF1 (USP1 Associated Factor 1). UAF1 contains 677 amino acids and harbors 7 or 8 potential WD40-repeats in the N-terminal half and a predicted coiled coil structure in the C-terminal half. Tertiary structure prediction using the Phyre software, available on the world wide web at sbg.bio.ic.ac.uk/.about.phyre, suggests the presence of a complete propeller structure comprised by the WD40 repeats. The intensities of Coomassie blue stained USP1 and UAF1 proteins in the SDS-PAGE were nearly identical, suggesting stoichiometric amounts of the two proteins in the complex and a possible functional relationship.

The protein subunits in the USP1 complex were analyzed by immunoblotting, using antibodies to the USP1 protein (Nijman et al. (2005) *Mol Cell* 17:331-9) and newly generated antibodies against the UAF1 protein. The results confirmed the presence of full length USP1, N-terminal USP1, and UAF1 in the USP1 complex, in good correlation with the Coomassie blue stain of the complex.

Flag-HA-tagged UAF1 was expressed in HeLa cells and the protein was immunoprecipitated with associated proteins. Immunoblotting of the immunoprecipitate revealed the presence of endogenous USP1 as well as its cleavage product, confirming the presence of a native USP1/UAF1 complex. The majority of USP1 protein in the HeLa cells was observed to exist as a protein complex with UAF1.

Example 4. Production of a Polyclonal Antibody to UAF1

A polyclonal rabbit antibody was raised against a fragment of the UAF1 protein consisting of amino acids 400-677. A 6×His-UAF1 (400-677) fusion protein was expressed in *E. coli* and purified over an NTA column. The purified protein was injected subcutaneously into a rabbit with Freund's complete adjuvant in the first injection and Freund's incomplete adjuvant for the following boost injections.

Example 5. Initial In Vitro Screening to Identify Small Molecule Inhibitors of USP1 Deubiquitinating Activity USP1/UAF1 protein complex serves as an excellent target for high throughput screening to identify small molecule inhibitors as radioprotective agents. A baculovirus mediated SF9 insect cell expression method has been developed for both USP1 and UAF1. The expressed proteins are purified by affinity, ion exchange, and gel filtration chromatography. Briefly, a baculovirus for USP1 and UAF1 was generated using the Bac-to-Bac baculovirus expression system (Invitrogen, CA). Full length USP1 contains an autocleavage site at residue 670-671, where cleavage occurs at GG after a Ubiquitin like motif. Huang et al. (2006) *Nat Cell Biol.* 8:1043-45. In order to purify the intact full length protein, two Glycine residues were mutated to Alanines using site directed mutagenesis (Stratagene). This modified full length USP1 clone was PCR amplified and subcloned into pFastBac-HT vectors (Invitrogen, CA) with N-terminal His tag.

USP1 Associated Factor 1 (UAF1) was also cloned into pFastBac vector, but without the N-terminal His tag. The clones were PCR verified and transformed into DH10Bac cells for blue-white colony selection. Bacmid DNA from the re-confirmed colony was extracted and presence of correct USP1 or UAF1 clones were confirmed by PCR amplification. The bacmid DNA were then transfected into SF9 cells using the Cellfectin reagent (Invitrogen, CA). P1 virus sets were collected following manufacturer's protocol and used to amplify P2 and P3 virus respectively. SF9 cells were co-infected with USP1 and UAF1 viruses to co-express these two proteins. A series of virus titer was used to optimize the expression level of USP1 and UAF1. Best expression of USP1 and UAF1 was observed with the virus titers of 1 µl in 2000 µl and 4000 µl of SF9 culture respectively. Expression level of these proteins at various time points after infection was also tested to determine optimum time of expression. Best expression was achieved at 60 hours after infection. Finally, SF9 suspension culture was infected at cell density 1.8 million/ml and grown at 28° C. on orbital shaker for 60 hours. After expression, cells were harvested at 500 g for 7 minutes, washed with 1×PBS, centrifuged again and stored at −80° C. for purification.

USP1 and UAF1 complex was initially purified by Ni-NTA affinity purification. SF9 cells were resuspended in a pre-chilled lysis buffer containing 50 mM Tris pH 8.0, 200 mM NaCl, 10 mM imidazole, 10 mM β-mercaptoethanol, 10% glycerol and 0.2% Triton X. After sonication, the cell lysate was centrifuged at 20,000 r.p.m. for 45 minutes at 4° C. Ni-NTA resin equilibrated in the lysis buffer and added to the soluble supernatant from the whole cell lysate. 2-3 ml of resin was added to per 2 liter of SF9 culture. The resin was incubated with mixing for 1 hour at 4° C. and spun down resin at 500×g for 5 min. After carefully removing the supernatant, the Ni-NTA resin was re-suspended in lysis buffer to wash out any unbound proteins. After spinning down the resin again, it was resuspended in wash buffer containing 50 mM Tris pH 8.0, 150 mM NaCl, 20 mM imidazole, 10 mM β-mercaptoethanol, 10% glycerol, and 1% Triton X. After spinning down the resin again, it was washed twice with wash buffer containing 50 mM Tris pH 8.0, 1000 mM NaCl, 20 mM imidazole, 10 mM β-mercaptoethanol, and 10% glycerol, followed by a final wash with buffer containing 50 mM Tris pH 8.0, 100 mM NaCl, 20 mM imidazole, 10 mM β-mercaptoethanol, and 10% glycerol. The bound USP1/UAF1 complex was eluted slowly from the column by elution buffer containing 50 mM Tris pH 8.0, 100 mM NaCl, 250 mM imidazole, 10 mM β-mercaptoethanol, and 10% glycerol. At this stage, eluted USP1/UAF1 complex was further purified by ion exchange chromatography using Q-sepharose column. The purified protein complex was further purified by gel filtration using S-200 column. Final buffer to be used in gel filtration column contained 50 mM Tris pH 8.0, 100 mM KCl, 5 mM DTT, and 0.1 mM EDTA. After final purification, quality of the protein was checked by SDS-PAGE and Coomassie blue staining. Finally, USP1/UAF1 concentration was measured by Bradford assay (BioRad, Calif.). 11 mg of protein complex were purified from 2 liter SF9 culture at a final concentration of 0.77 mg/ml.

In order to develop a highly sensitive assay with easy readout for high throughput detection, the fluorogenic compound Ubiquitin-7-amido-4-methylcoumarin (AMC-Ub, Boston Biochem) was used as a substrate for USP1/UAF1 enzyme complex. USP1 catalyzes the cleavage of AMC-Ub, releasing free AMC moiety, which leads to increase in fluorescence emission at 460 nm ($\lambda_{ex}$=380 nm). Dang et al. (1998) *Biochemistry* 37:1868-79. Catalytic activity towards AMC-Ub increases 35 fold compared to USP1 enzyme alone. Initial enzyme assay development was performed in 96-well plates with 100 µl reaction volume containing 20 mM HEPES-KOH, 0.1 mg/ml ovalbumin (Sigma), 0.5 mM EDTA, and 10 mM DTT. 2.5 nM USP1/UAF1 enzyme complex was mixed with the reaction buffer, incubated at 37° C. for 10 minutes and then 0.3 µM AMC-Ub was added. Fluorescence was measured using a Fluostar Galaxy Fluorometer (BMG Labtech Inc.).

Ubiquitin aldehyde (Al-Ub) is a potent covalent inhibitor of deubiquitinating enzymes, and it inhibits the enzyme by covalently attaching to the active site. There is a sharp decrease in enzyme activity upon incubation of USP1/UAF1 complex with 25 nM of Al-Ub. The significant decrease in signal upon Al-Ub can easily be detected in high throughput data collection and data interpretation. Hence, Al-Ub can be used as positive control for inhibition in screening assays, including high throughput screening, and any potential inhibition signal can be compared to this control.

Once the preliminary enzyme assay was established in 96-well format, it was optimized for 384 wells for high throughput screening (HTS) of inhibitors. The major points to be considered were the volume of the reaction and amount of AMC-Ub substrate to be used in the assay. Since the price of AMC-Ub is very high, in order to make it a feasible assay for HTS, lowest workable amount of the AMC conjugate was used. Reaction volume was minimized to 30 µl in order to meet the recommendation of ICCB-L screening facility (Harvard). In the preliminary optimization experiment, a series of pilot experiments were performed with varying AMC-Ub concentrations (0.025 µM to 0.2 µM), along with the varying concentration of USP1/UAF1 complex (0.2 nM to 3.2 nM). This concentration grid was performed in 384-well plates (Corning, 3711) using the automated liquid handler present at ICCB-L screening facility. After incubating the enzyme and buffer at 37° C. for 10 minutes, AMC-Ub was added and fluorescence emission at 460 nm ($\lambda_{ex}$=380 nm) was measured in an automated plate reader Envision 2 (Perkin Elmer). Fluorescence reading for all time points up to one hour was noted and the data for different AMC-Ub concentration range was plotted with each USP1/UAF1 enzyme complex concentration. Comparison of fluorescence emission in each set showed the minimum optimal AMC-Ub concentration required with optimum USP1/UAF1 concentration to obtain significant increase in signal compared to the baseline. Based on the results, 0.1 µM AMC-Ub concentration along with 1.6 nM USP1/UAF1 concentration produced significantly increased signal from the baseline and these optimum concentrations were used for HTS. So by this optimization AMC-Ub concentration was reduced 3 times (0.3 µM to 0.1 µM) and volume of the reaction was reduced 3.33 times (100 µl to 30 µl). Taken together, the overall use of the substrate was reduced 10 times by doing this optimization (3×3.33). Unlike single enzyme assay, only one time point can be collected in HTS with thousands of compound screen. This optimization step also shows the desirable time point to read fluorescence signal is 15 minutes after addition of AMC-Ub, as this is before the reaction reaches the saturation.

After large scale expression-purification of USP1/UAF1 protein complex, high throughput screening was performed. Buffers and USP1/UAF1 complex were added into 384-well plates (Corning, black 3711) using automated liquid handling robot Bio-Tek Microfill (Bio-Tek Instruments Inc., VT). This was followed by addition of compounds to the plate wells using pin transfer robotic system. This includes a custom designed Seiko Cartesian robot with pin arrays (V & P Scientific Inc.) and Zymark Twister II robotic arm to stack and transfer compound plates and assay plates. In this step, 100 µL of the compounds (in DMSO) from compound library plates was added to the 384-well assay plates. After incubating the assay plates at 37° C. for 10 minutes, desired volume of AMC-Ub was added by the automated liquid handler. Finally, fluorescence emission at 460 nm ($\lambda_{ex}$=380 nm) was measured in an automated plate reader Envision 2 (Perkin Elmer, Mass.). The Z' factor for the assay was calculated (Zhang et al. (1999) *J Biomol Screen* 4:67-73) and, if required, the assay was further optimized until Z'>0.5.

The HTS assay was run using the ICCB-L Biomol bioactive library (Harvard Medical School, Boston, Mass.). ICCB-L has a collection of over 150,000 compounds in their compound library, which consists of known bioactive libraries, natural product libraries, and commercial libraries such as ChemDiv, ChemBridge, etc. Known bioactive libraries containing Biomol ICCB known bioactives, NINDS, and Prestwick collections were tested first for potential inhibitors. This set of the library contains many FDA-approved drugs and the compounds are known to exhibit low toxicity and high cellular retention, making them excellent targets for further cell-based assay. The reactions were performed using automated instruments as described above. Among two bioactive libraries tested, three compounds, β-lapachone, Biomol AP401 (propidium iodide), and RK-682, were previously shown to have substantial low fluorescence signal in the range of Al-Ub-treated positive control sets. US 2008/0167229 A1. Identification of these compounds by high throughput screening established the validity of the experimental setup.

Results.

Four additional small molecule inhibitors of USP1 deubiquitinating activity were identified from a screen of approximately 150,000 compounds. The compounds so identified included the following:

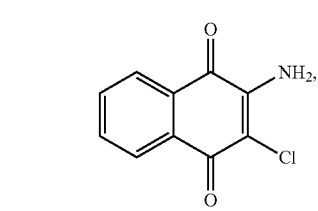

Formula III (933)

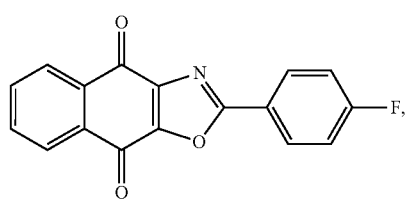

Formula IV (527)

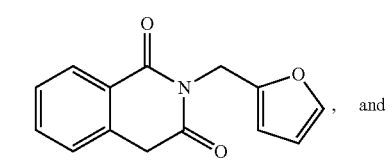

Formula V (947)

, and

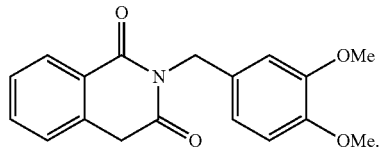

Formula VI (009)

Example 6. Additional In Vitro Screening to Characterize Small Molecule Inhibitors of USP1 Identified in Initial Screening Hits from the initial screening were analyzed further in secondary screening. In this step, the compounds were re-tested for inhibition using the AMC-Ub in vitro enzyme assay. After reconfirming inhibition, different concentration range of the inhibitors were tested to show dose dependency of inhibition and IC50 calculation.

Figure 2:
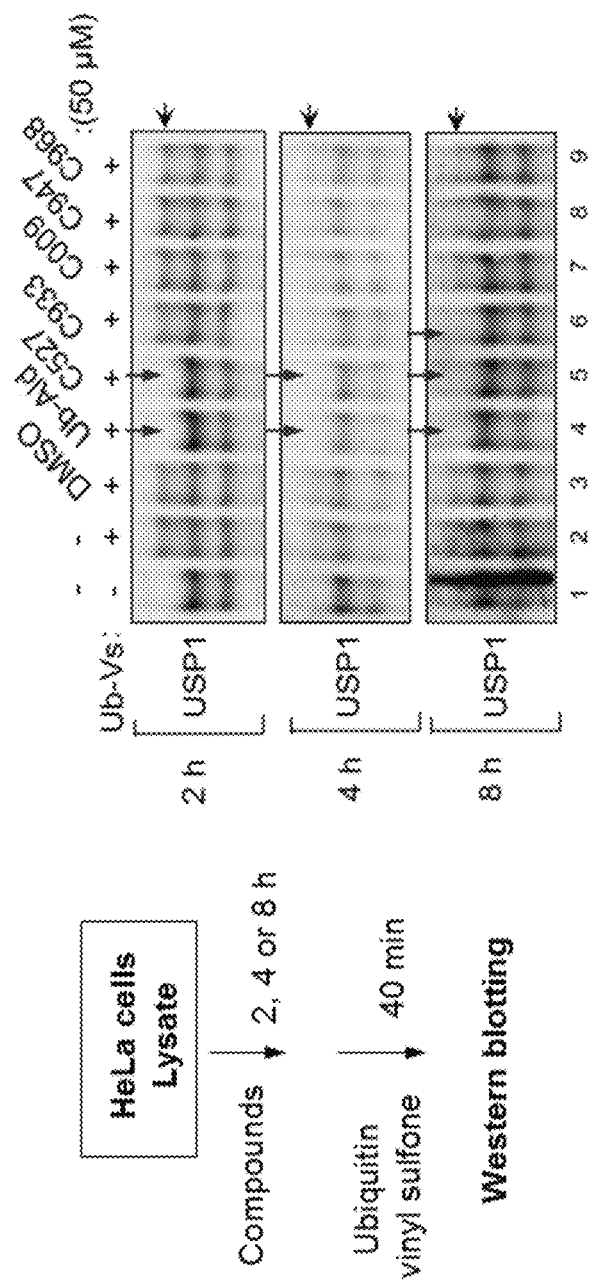
FIG. 2 is a composite figure depicting small molecule inhibition of USP1 activity in vitro. Ub-Vs, ubiquitin vinyl sulfone; Ub-Ald, ubiquitin aldehyde; LDN_0082527 and C527, the compound of Formula IV (527); C933, the compound of Formula III (933); C009, the compound of Formula VI (009); C947, the compound of Formula V (947).

In one set of experiments, HeLa cells were incubated in the presence of 50 µM of selected inhibitors including the compound of Formula III (933) and the compound of Formula IV (527) for 2, 4, or 6 hours, followed by cell lysis. Ub-aldehyde (Ub-Ald, a known USP1 inhibitor) was used as a positive control, and dimethysulfoxide (DMSO) was used as a negative control. Lysates were incubated with the Ub-vinyl sulfone (Ub-Vs) reagent for 40 minutes. Proteins were electrophoresed on SDS-PAGE, transferred to nitrocellulose, and immunoblotted with the anti-USP1 antibody. Results are shown in FIG. 2.

Results.

Ub-aldehyde blocked Ub-Vs conjugation of USP1 (lane 4), whereas DMSO alone did not block conjugation of USP1 (lane 3). Of five putative USP1 inhibitors evaluated (lanes 5-9), the C527 compound was a potent inhibitor of deubiquitinase activity.

IC50 values for compounds of Formulas III-VI, determined following 4 hour preincubation, are shown in Table 1.

TABLE 1

| Compound | IC50 (nM) |
|---|---|
| Formula III (933) | —[a] |
| Formula IV (527) | 134 |
| Formula V (947) | 7,500 |
| Formula VI (009) | 2,400 |

[a]No data

Figure 3:
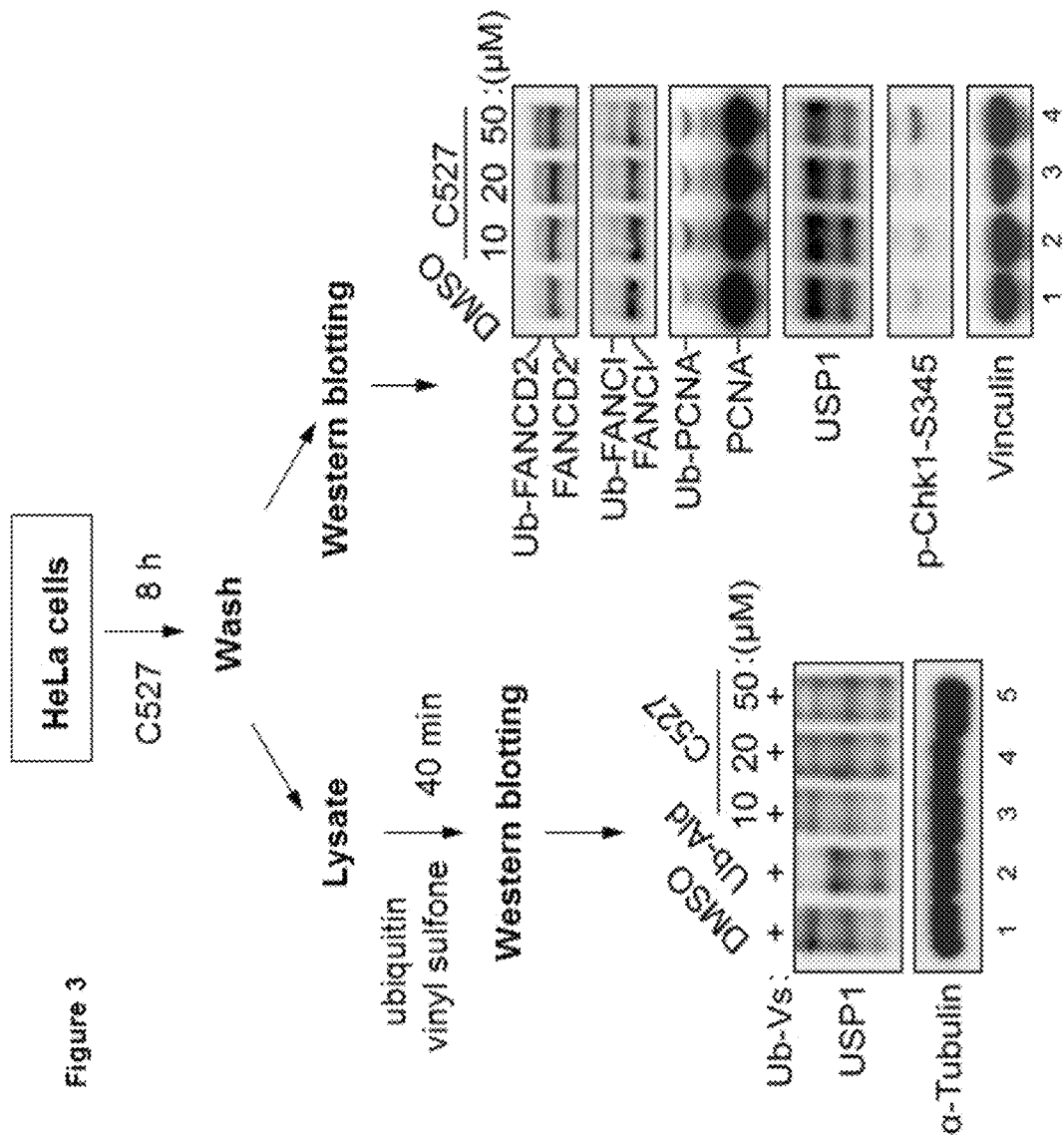
FIG. 3 is a composite figure depicting dose-dependent blockade of USP1 activity (lanes 1-5) and dose-dependent accumulation of ubiquitinated FANCD2 and FANCI in response to the compound of Formula IV (527). C527, the compound of Formula IV (527); Ub-Vs, ubiquitin vinyl sulfone; Ub-Ald, ubiquitin aldehyde.

Example 7. Cell-Based Screening to Further Characterize Small Molecule Inhibitors of USP1 Identified in In Vitro Screening Candidate USP1 inhibitors from initial and secondary screens were then used in cell-based assays to look for USP1 inhibition in vivo using levels of FANCD2-Ub and PCNA-Ub as biomarkers for inhibition. For the cell-based assay, cells were treated with the candidate compounds and levels of monoubiquitinated FANCD2 and PCNA were tested both with and without DNA damage. USP1 inhibition was detected as high level of endogenous monoubiquitinated FANCD2 and PCNA. For this assay HeLa and HEK293T cells were treated with selected concentrations of these compounds and grown in Dulbecco's modified Eagle's medium supplemented with 15% heat-inactivated fetal calf serum in a humidified 5% $CO_2$ incubator at 37° C. Damage was induced by both UV irradiation using Stratalinker (Stratagene) and treatment with mitomycin C (MMC, Sigma). After cell lysis, levels of monoubiquitinated FANCD2 and PCNA in whole cell lysate was tested by immunoblotting with anti-FANCD2 antibody (sc-20022; Santa Cruz Biotechnology) and anti-PCNA antibody (sc-56; Santa Cruz Biotechnology). Protection from chromosome aberrations were also tested in UV/MMC-damaged cells treated with candidate USP1 inhibitors using standard chromosome breakage assay. Yang et al. (2001) *Blood* 98:3435-40. Representative results are shown in FIG. 3.

Results.

HeLa cells were incubated with the compound of Formula IV (527) for eight hours, followed by cell lysis and incubation of protein extract with Ub-vinyl sulfone. Increasing concentrations of the compound of Formula IV (527) resulted in a dose-dependent blockade of USP1 deubiquitinase activity (lanes 3, 4, 5). Increasing concentrations of the compound of Formula IV (527) also resulted in a dose-dependent increase in FANCD2-Ub levels and FANCI-Ub levels (lanes 7, 8, 9).

Figure 4:
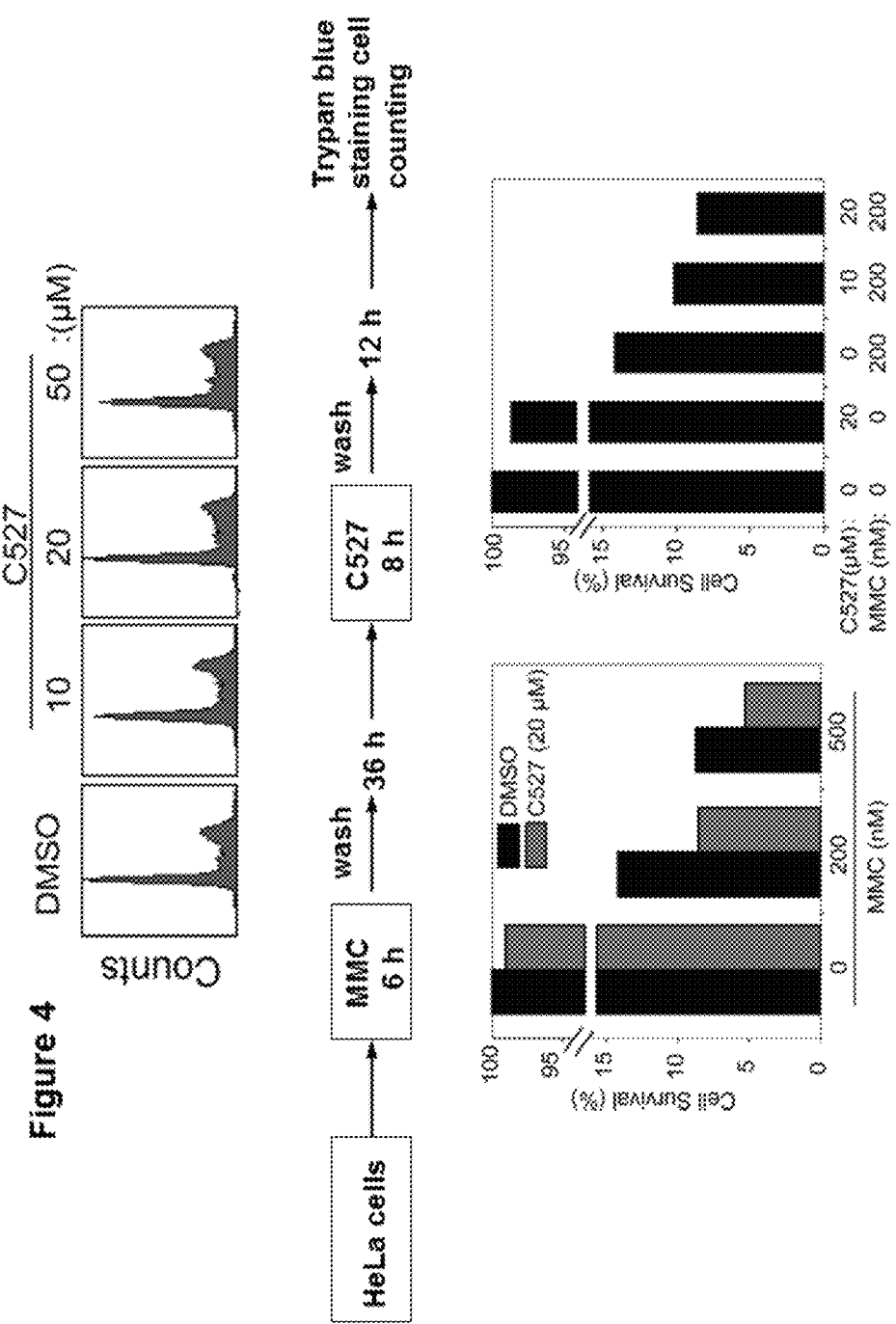
FIG. 4 is a composite figure depicting sensitization of HeLa cells to the DNA cross-linking agent mitomycin C by the compound of Formula IV (527). C527, the compound of Formula IV (527); MMC, mitomycin C.

Example 8. USP1/UAF1 Inhibitor Sensitizes HeLa Cells to the DNA Crosslinking Agent Mitomycin C HeLa cells were pretreated for six hours with selected concentrations (0, 200, or 500 nM) of mitomycin C (MMC), washed, then exposed to selected concentrations (0, 10, or 20 µM) of the compound of Formula IV (527) for eight hours. Cell survival was measured by redox dye. Results are shown in FIG. 4.

Results.

Pretreatment with the compound of Formula IV (20 micromolar) resulted in sensitization of the HeLa cells to the cytotoxic effects of MMC.

Example 9. C527 Inhibits USP1/UAF1 in a Time-Course and Dose-Dependent Manner

Figure 5:
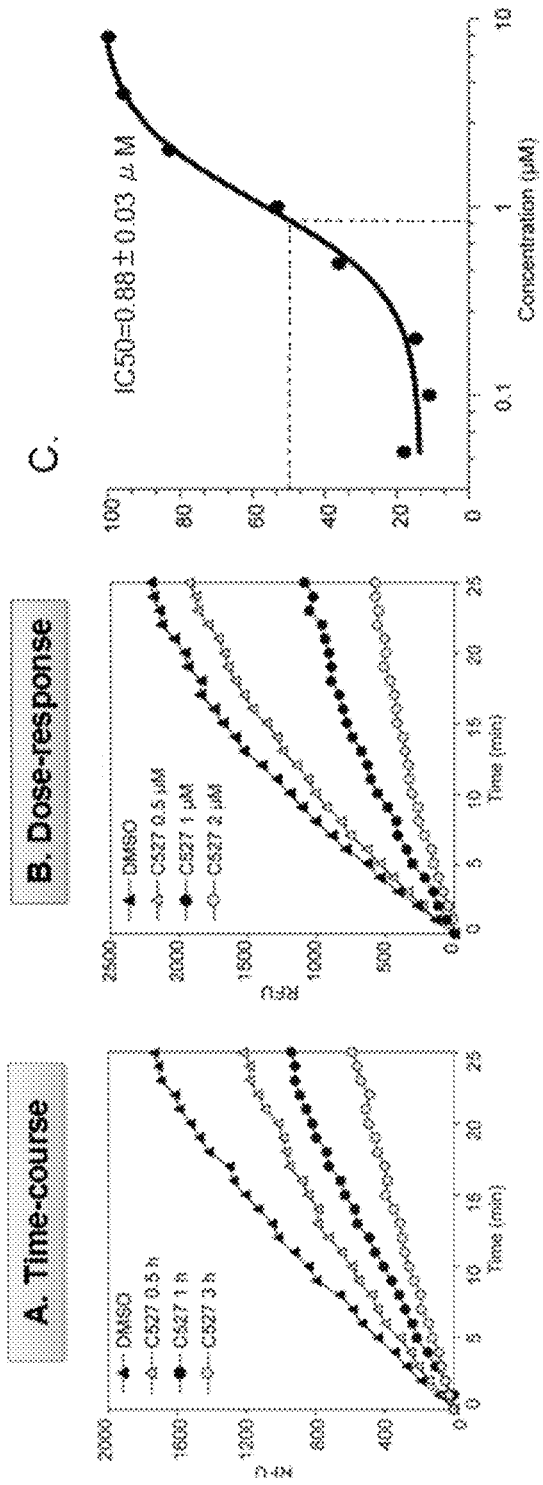
FIG. 5 is a composite figure depicting time-course and dose-dependent C527 inhibition of USP1/UAF1 activity.

The ability of C527, the compound of Formula IV (527) to inhibit USP1/UAF1 in a time-course and dose-dependent manner (FIG. 5) was confirmed using ubiquitin-AMC (Ub-7-amido-4-methylcoumarin), another ubiquitin derivative similar to Ub-Rhodamine (Ub-Rho) but having a different emission wavelength, as substrate. Pretreatment of USP1/UAF1 with a single dose of C527 (1 uM) for variable time periods resulted in a serial increase in inhibition of DUB activity (i.e., fluorescence) (FIG. 5A). Treatment for 2 h with an increase in dose of C527, ranging from 0.5 to 2 µM, resulted in a dose-dependent decrease in DUB activity (FIG. 5B). Based on these results, the IC50 of C527 for the USP1/UAF1 complex was 0.88±0.03 µM (FIG. 5C).

Example 10. C527 is a Pan-Deubiquitinating Enzyme Inhibitor In Vitro

Figure 6:
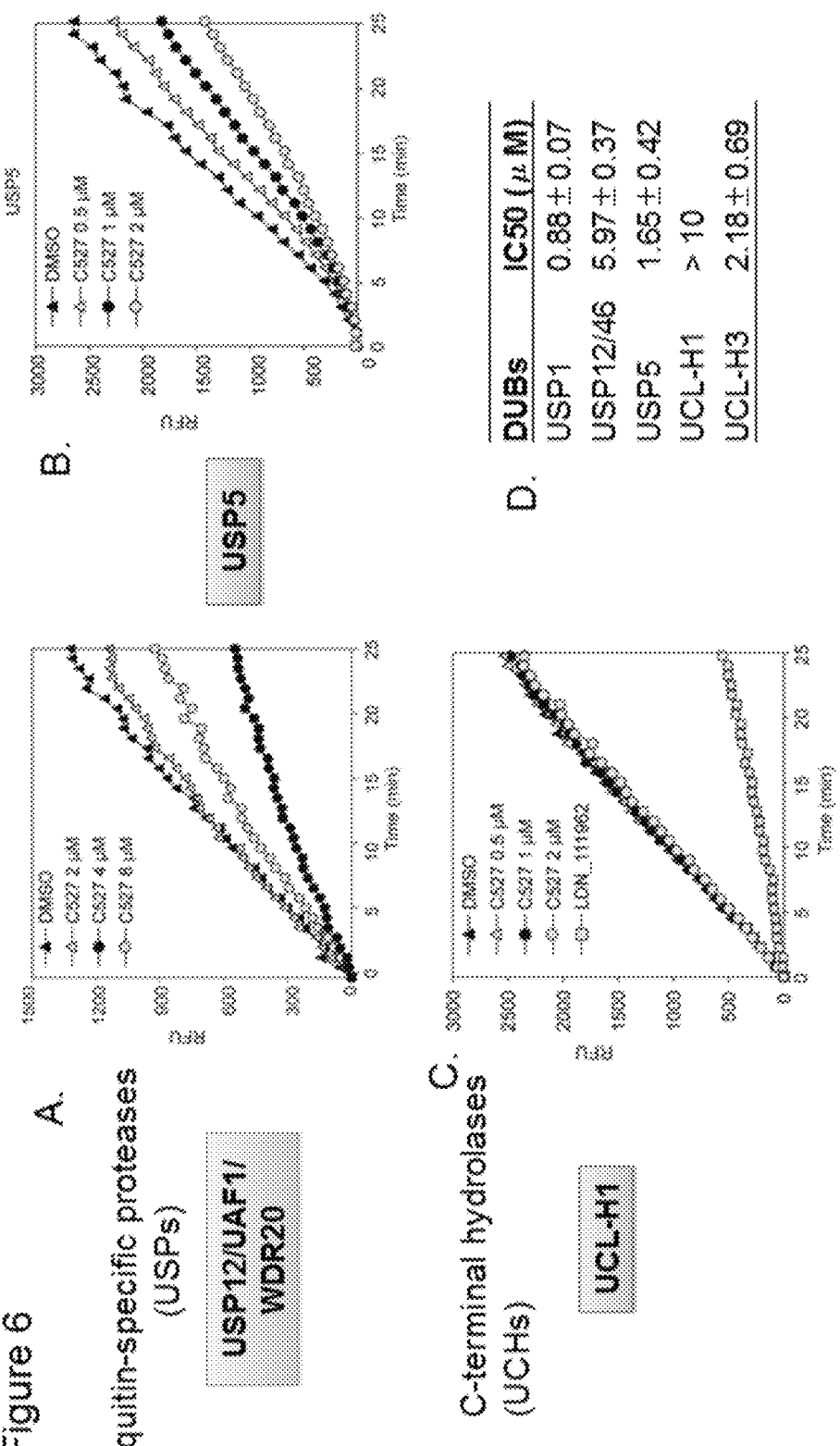
FIG. 6 is a composite figure showing that C527 is a pan-deubiqutinating enzyme inhibitor in vivo. Ubiquitin-AMC assay was performed using purified (FIG. 6A) USP12/UAF1/WDR20 (FIG. 6B) USP5 and (FIG. 6C) UCH-L1. Enzymes were incubated with DMSO or C527 at indicated concentrations for 3 h, followed by the addition of Ub-AMC at 0.5 μM final concentration. The fluorescence at 535 nM was measured to indicate the enzymatic activity.

To examine the specificity of C527 in USP1/UAF1 inhibition, its ability to inhibit other DUB enzymes in vitro was examined. It has been recently showed that UAF1 stimulates not only USP1, but also two other DUB enzymes, USP12 and USP46 (Cohn M A, Kee Y, Haas W, Gygi S P, D'Andrea A D. UAF1 is a subunit of multiple deubiquitinating enzyme complexes. J Biol Chem. 2009; 284:5343-5351). Moreover, the active complex of USP12 contains an additional WD40 subunit (WDR20). C527 also inhibited the DUB activity of the USP12/UAF1/WDR20 complex, as well as the USP5 enzyme in vitro (FIGS. 6A and 6B). However, the IC50 of C527 for these DUB enzymes was slightly higher (FIG. 6D). UCH-L1 and UCH-L3 are members of a different subclass of deubiquitinating enzymes, referred to as the ubiquitin-carboxy terminal hydrolases (Mermerian A H, Case A, Stein R L, Cuny G D. Structure-activity relationship, kinetic mechanism, and selectivity for a new class of ubiquitin C-terminal hydrolase-L1 (UCH-L1) inhibitors. Bioorg Med Chem Lett. 2007; 17:3729-3732). Interestingly, C527 had considerably less inhibitory effect on these deubiquitinating enzymes, even though they are also cysteine proteases. Taken together, C527 is a pan-deubiquitinating enzyme inhibitor in vitro, though it has some specificity for the USP subfamily of DUBs, compared to the UCH subfamily.

Figure 7:
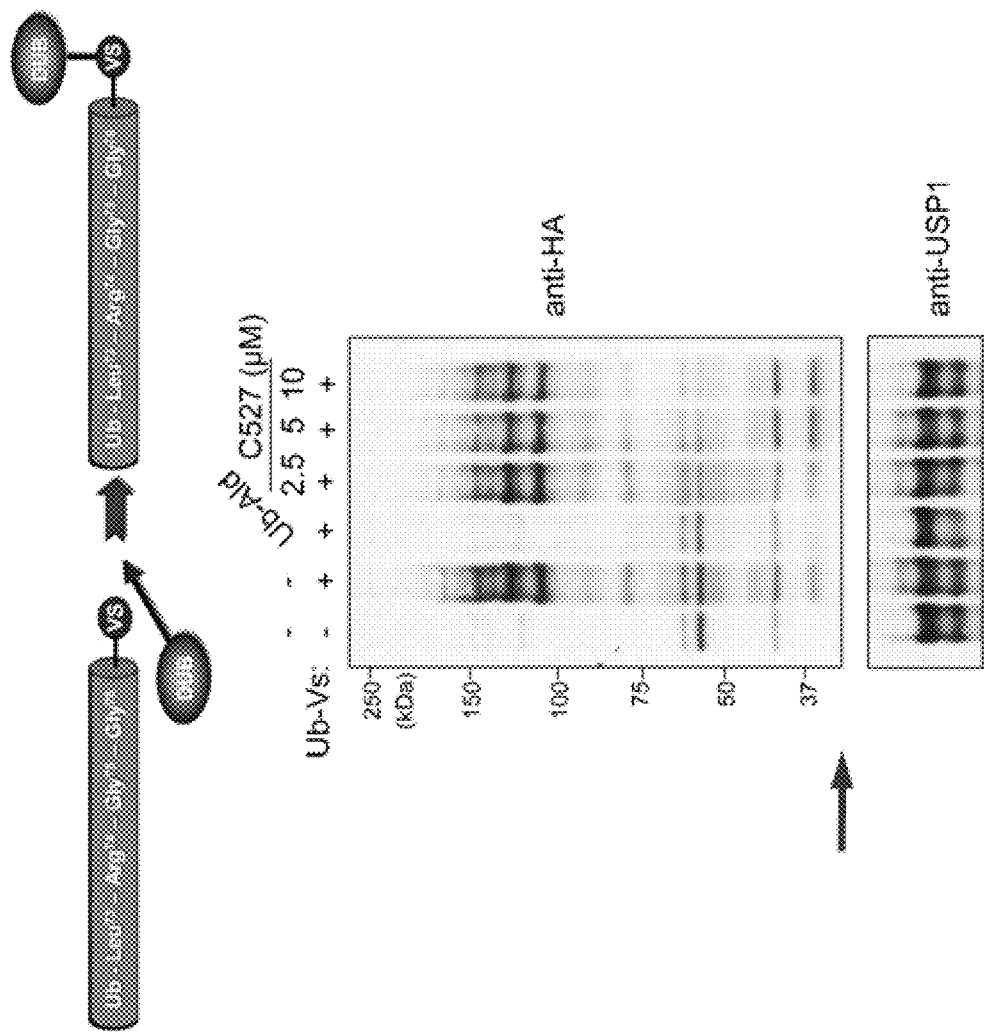
FIG. 7 is a composite figure depicting preferential inhibition of the activity of native USP1/UAF1 by C527. HeLa cell extracts were incubated with ubiquitin-aldehyde (Ub-Ald, 5 μM) or C527 at indicated concentrations for 4 h, followed by the addition of 0.5 μM Ub-Vs for 40 min. The reaction was split into two aliquots and subjected to immunoblotting for HA or USP1, respectively.

The ability of C527 to inhibit the deubiquitinating activity of native USP1 complexes derived from human cells was determined next (FIG. 7). For this purpose, the HA-tagged ubiquitin-VS, an affinity reagent known to covalently modify and trap active DUB enzymes in cell extracts was used. Cell extracts prepared from HeLa cells were pretreated with increasing concentrations of C527 for 4 h, followed by the incubation with Ub-VS for 40 min at 30° C. The enzymatic activity of endogenous DUBs was indicated by the conjugation of Ub-VS, detected as HA-labeling (see FIG. 7, high molecular weight bands). Solvent vehicle treated cell extracts showed increased enzymatic activity of endogenous DUBs, as indicated by a whole panel of HA-labeling at different molecular weight. Ub-VS conjugation was inhibited by ubiquitin-aldehyde (Ub-Ald), a non-specific inhibitor of DUBs (lane 3). In contrast, C527 failed to inhibit the Ub-VS labeling of other endogenous DUB enzyme complexes but did inhibit USP1 binding to Ub-VS in the same reaction in a dose-dependent manner. These data indicate that C527 has a preferential inhibition of the native USP1, compared to other native DUB s in the extract.

Example 11. C527 Impairs Homologous Recombination Repair

Recent studies have indicated that the Fanconi Anemia pathway is required for optimal homologous recombination (HR) repair (Nakanishi K, Yang Y G, Pierce A J, et al. Human Fanconi anemia monoubiquitination pathway promotes homologous DNA repair. Proc Natl Acad Sci USA. 2005; 102:1110-1115). Disruption of FANCD2 monoubiquitination or of USP1 activity (Oestergaard V H, Langevin F, Kuiken H J, et al. Deubiquitination of FANCD2 is required for DNA crosslink repair. Mol Cell. 2007; 28:798-809; Kim J M, Parmar K, Huang M, et al. Inactivation of murine Usp1 results in genomic instability and a Fanconi anemia phenotype. Dev Cell. 2009; 16:314-320) results in decreased HR. A gene conversion assay was used to examine the effect of C527 on cellular HR activity (FIG. 8A). Interestingly, C527 caused a dose-dependent decreased in gene conversion, based on the measurement of cellular GFP in this assay, and inhibition occurred in the 0 to 5 µM range (FIG. 8A). In contrast, C527 did not inhibit non-homologous end joining (NHEJ) activity under the same condition (FIG. 8B).

Figure 8C:
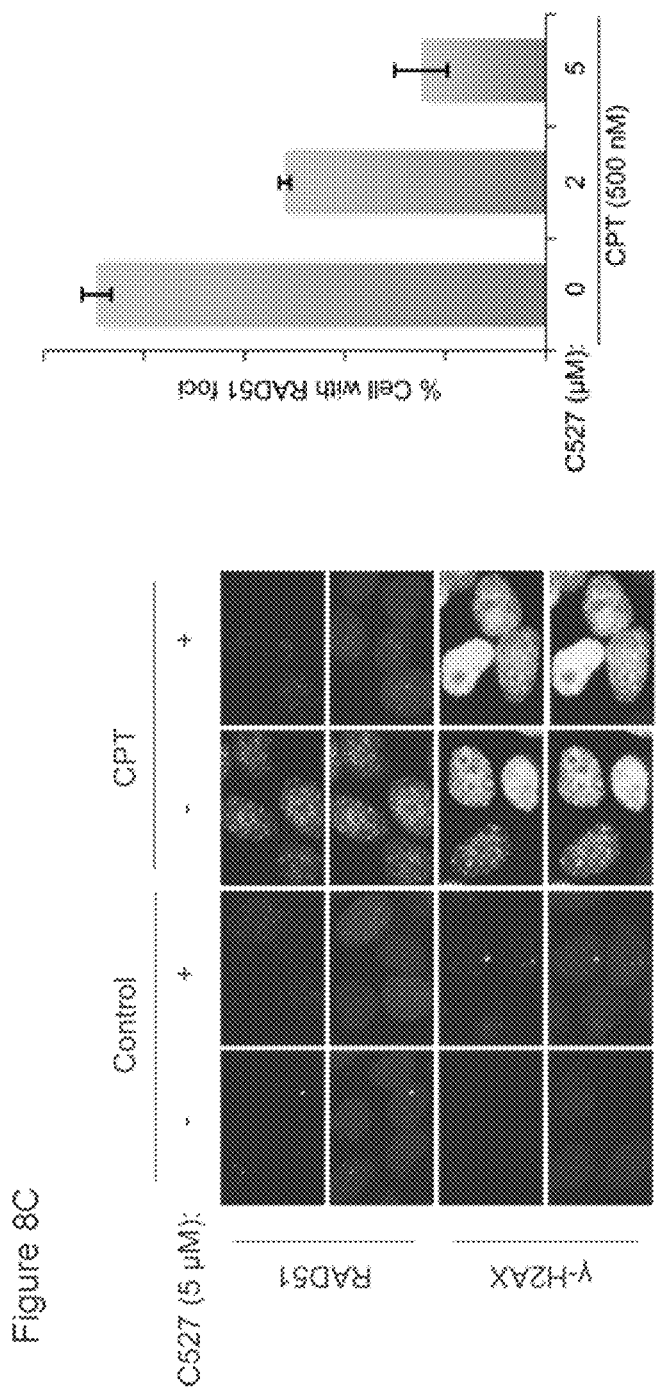
FIG. 8C shows that C527 inhibits camptothecin-induced RAD51 foci formation. HeLa cells were pre-treated with DMSO or C527 at the indicated concentration and then exposed to camptothecin (CPT) for 1 hr. RAD51 foci were detected using immunofluorescence.

To confirm that the C527 treatment caused HR defect, RAD51 foci formation, another surrogate marker of cellular HR activity, was tested (FIG. 8C). Camptothecin activated the assembly of RAD51 and H2AX foci. C527 treatment inhibited RAD51 foci formation but had a non-detectable effect on H2AX foci formation. Taken together, these results further indicate that C527 has HR-inhibitory activity.

Figure 9:
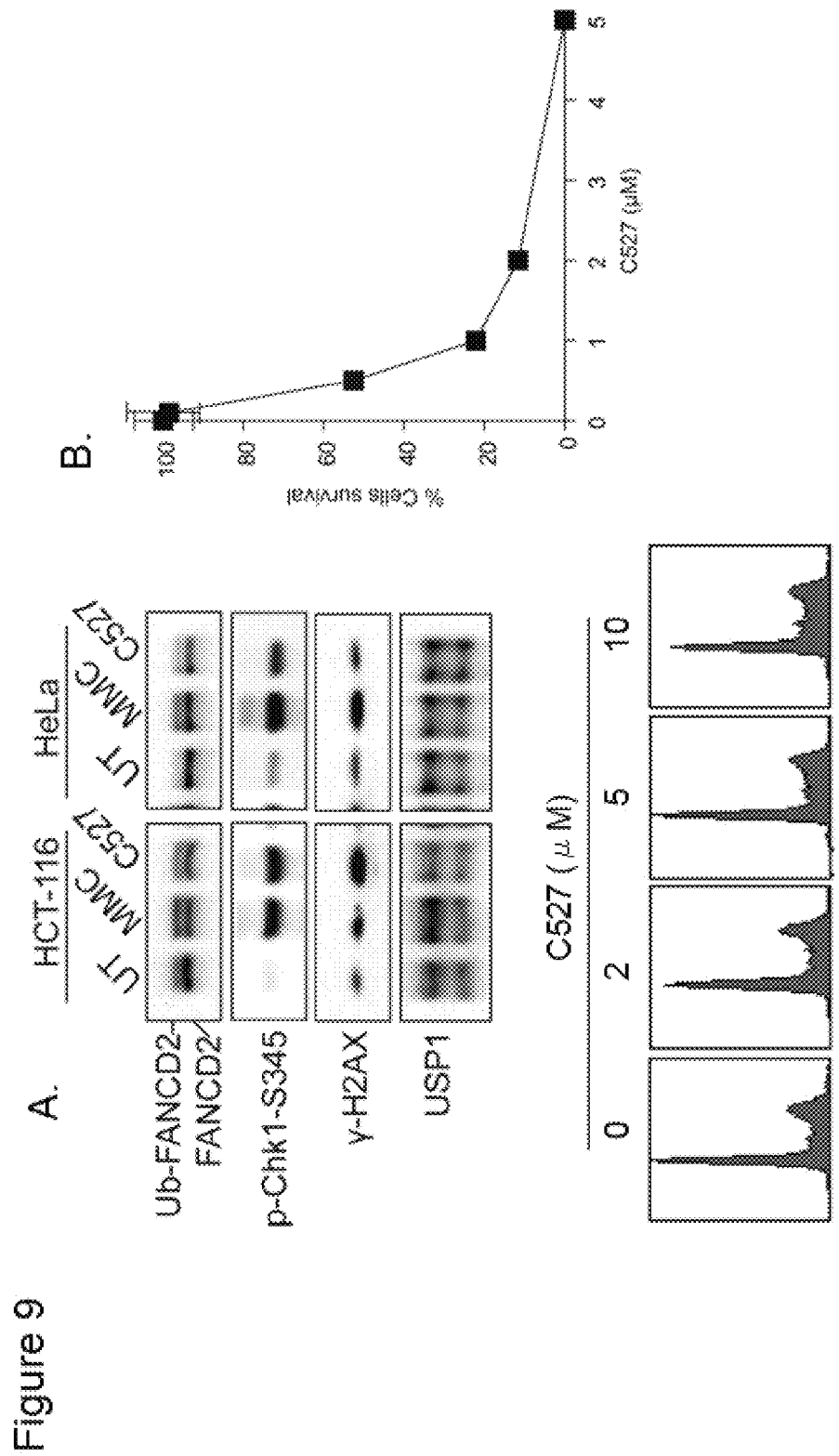
FIG. 9 is a composite figure showing that C527 causes DNA damage and inhibits the proliferation of tumor cells.

Example 12. C527 Causes DNA Damage and Inhibits the Proliferation of Tumor Cells Impaired HR integrity may lead to genotoxic effect. Genotoxic agents are known to directly activate DNA damage response pathways, resulting in FANCD2 monoubiquitination and CHK1 phosphorylation (FIG. 9A). The results indicate that C527, like the genotoxic crosslinking agent MMC, can activate markers of the DNA damage response. Accordingly, C527 treatment inhibited cell proliferation as assessed using clonogenic assay (FIG. 9B).

Example 13. C527 Sensitizes Tumor Cells to DNA Damaging Agents

Figure 10:
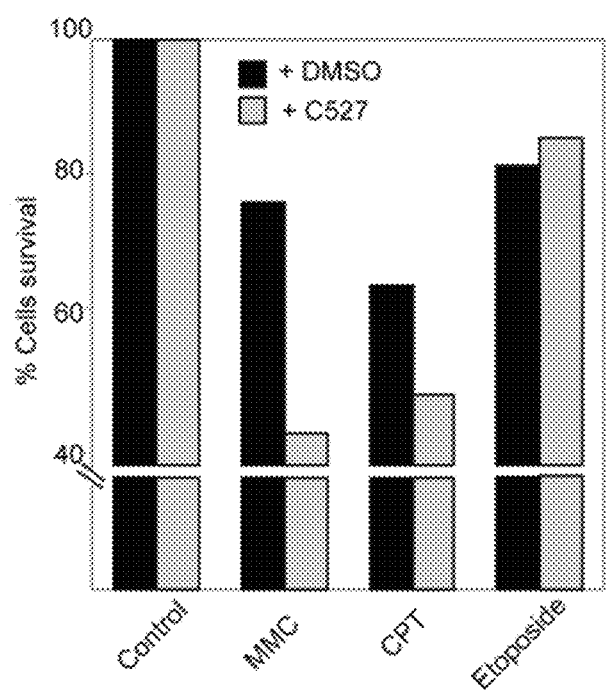
FIG. 10 is a composite figure showing that C527 sensitizes tumor cells to DNA damaging agents. HeLa cells were plated in 96-well plates and treated with 1 μM C527 for 24 h, followed by treatment with mitomycin C (MMC, 0.25 μM), camptothcin (CPT, 0.1 μM), or etoposide for 4 more days. Cell viability was assessed using the MTT assay.

Inhibitors of the FA-BRCA pathway are known to sensitize tumor cells to the cytotoxic effects of ICL-indicating agents. Specifically, it is known that proteasome inhibitors block FANCD2 monoubiquitination, perhaps through depletion of intracellular pools of free ubiquitin, resulting in inhibition of HR repair (Chirnomas D, Taniguchi T, de la Vega M, et al. Chemosensitization to cisplatin by inhibitors of the Fanconi anemia/BRCA pathway. Mol Cancer Ther. 2006; 5:952-961). The ability of C527 to sensitize pretreated human cells to MMC or to other agents was tested. C527 sensitized cells to MMC and to CPT, consistent with its ability to specifically inhibit HR in cells (FIG. 10).

DNA Repair inhibitors have recently emerged as a novel class of anti-cancer agents. Conventional anticancer agents, such as the alkylating agents busulfan and cyclophosphamide, kill cancer cells by causing DNA damage. Tumors can become resistant to conventional therapy by amplifying DNA repair pathways. DNA repair inhibitors, such as the newly developed PARP inhibitors, block DNA repair and sensitize tumor cells to conventional agnets.

There are several DNA repair pathways in human cells, and each pathway deals with a specific set of DNA lesions. The Fanconi Anemia (FA-BRCA) pathway, regulates homologous recombination repair and is require for interstrand DNA crosslink repair. A DNA repair inhibitor for this pathway is expected to sensitize tumor cells to crosslinking agents, such as cisplatin and mitomycin C.

Several enzymatic steps comprise the FA-BRCA pathway, and each step is a potential target for inhibitor development. Critical catalytic events in the FA-BRCA pathway include 1) the E3 ligase dependent monoubiquitination of FANCD2 and 2) the USP1-dependent deubiquitination of FANCD2-Ub. Disruption of either enzymatic step results in cisplatin sensitization.

Recent studies have identified small molecule inhibitors of FANCD2 monoubiquitination, and these compounds are currently in preclinical development (curcumin and proteasome inhibitor). Small molecule inhibitors of the FA-BRCA pathway can block HR repair and sensitize tumors to DNA crosslinking agents such as cisplatin. The results described herein demonstrate that C527 can inhibit USP1/UAF1 in vitro in a dose-dependent manner. Cells exposed to C527 exhibited reduced USP1 activity, increased monoubiquitinated FANCD2 levels, and a defect in homologous recombination repair. C527 also enhanced the cellular sensitivity of cancer cells to mitomycin C and camptothecin but not to etoposide treatment. The identification of this lead inhibitor against the USP1/UAF1 complex provides a structural basis for further development of new anticancer drugs.

Example 14. In Vivo Activity of C527

Bortezomib (Velcade) has been shown to inhibit the FA-BRCA pathway. Preliminary breast cancer xenograft studies with one HR pathway-proficient breast tumor line have been conducted. Bortezomib inhibited the FA/BRCA pathway and the combination of Velcade plus PARP inhibitor (ABT-888) resulted in enhanced killing of this cell line in vivo, compared to either agent alone (data not shown)

Nude mice bearing MDA-MB-231 tumor xenografts are treated with either vehicle control, ABT-888 (25 mg/kg B.W), cisplatin, C527 or combination of ABT-888 or cysplatin and C527. It is anticipated that C527 will have homologous recombination (HR)-inhibiting activity in vivo, and will synergize with PARP inhibitor and/or Cisplatin in vivo.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A method for treating a subject having a breast cancer or an ovarian cancer, comprising:

administering to a subject having breast cancer or ovarian cancer in need of such treatment a small molecule inhibitor of ubiquitin specific protease 1 (USP1) according to Formula I:

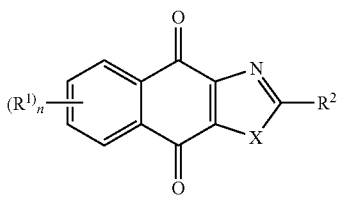

Formula I wherein
X is O or S;
n is 0, 1, 2, 3, or 4;
each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^A$; —$C(=O)R^A$; —$C(=O)N(R^A)_2$; —$CO_2R^A$; —CN; —SCN; —$SR^A$; —$SOR^A$; —$SO_2R^A$; —$NO_2$; —$N_3$; —$N(R^A)_2$; —$NHC(=O)R^A$; —$NR^AC(=O)N(R^A)_2$; —$OC(=O)OR^A$; —$OC(=O)R^A$; —$OC(=O)N(R^A)_2$; —$NR^AC(=O)OR^A$; or —$C(R^A)_3$; wherein each occurrence of $R^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^2$ is hydrogen; cyclic or acyclic, substituted or unsubstituted, branched or unbranched aliphatic; cyclic, substituted or unsubstituted, heteroaliphatic; substituted or unsubstituted, branched or unbranched acyl; substituted or unsubstituted aryl; substituted or unsubstituted heteroaryl; —$OR^B$; —$C(=O)R^B$; —$C(=O)N(R^B)_2$; —$SOR^B$; —$NHC(=O)R^B$; —$NR^BC(=O)N(R^B)_2$; or —$C(R^B)_3$;

wherein each occurrence of $R^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and wherein when $R^2$ is substituted aliphatic, each substituent is independently selected from an aryl moiety, a heteroaryl moiety, an arylalkyl moiety, a heteroarylalkyl moiety, an alkoxy moiety, an aryloxy moiety, a heteroalkoxy moiety, a heteroaryloxy moiety, an alkylthio moiety, an arylthio moiety, a heteroalkylthio moiety, a heteroarylthio moiety, —F, —Cl, —Br, —I, —OH, —NO$_2$, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, —C(O)R$_x$, —CO$_2$(R$_x$), —CON(R$_x$)$_2$, —OC(O)R$_x$, —OCO$_2$R$_x$, —OCON(R$_x$)$_2$, —N(R$_x$)$_2$, —S(O)$_2$R$_x$, —NR$_x$(CO)R$_x$, wherein each occurrence of R$_x$ is independently an aliphatic moiety, a heteroaliphatic moiety, an aryl moiety, a heteroaryl moiety, an arylalkyl moiety, or a heteroalkyl moiety;

or a pharmaceutically acceptable salt thereof, in an amount effective to treat the breast cancer or the ovarian cancer.

2. The method of claim 1, wherein the small molecule inhibitor of USP1 according to Formula I is the compound of Formula IV (527):

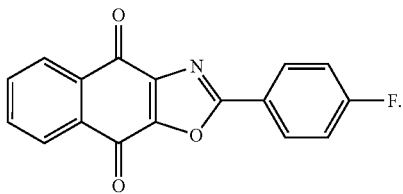

Formula IV (527)

3. The method of claim 1, further comprising administering to the subject a DNA cross-linking agent.

4. The method of claim 1, further comprising administering to the subject a poly (adenosine diphosphate (ADP)-ribose) polymerase (PARP) inhibitor.

5. The method of claim 1, further comprising administering to the subject a DNA cross-linking agent and a PARP inhibitor.

6. The method of claim 1, wherein X is O.

7. The method of claim 1, wherein n is 0.

8. The method of claim 1, wherein $R^2$ is substituted or unsubstituted phenyl.

9. The method of claim 8, wherein $R^2$ is phenyl substituted with halogen.

10. The method of claim 1, wherein the subject has breast cancer.

11. The method of claim 1, wherein the subject has ovarian cancer.

12. A method for treating a subject having a breast cancer or an ovarian cancer, comprising:

administering to a subject having breast cancer or ovarian cancer in need of such treatment a small molecule inhibitor of ubiquitin specific protease 1 (USP1) according to Formula I:

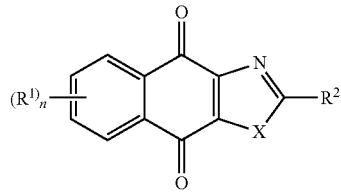

Formula I wherein

X is O;

n is 0, 1, 2, 3, or 4;

each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^A$; —C(=O)R$^A$; —C(=O)N(R$^A$)$_2$; —CO$_2$R$^A$; —CN; —SCN; —SR$^A$; —SOR$^A$; —SO$_2$R$^A$; —NO$_2$; —N$_3$; —N(R$^A$)$_2$; —NHC(=O)R$^A$; —NR$^A$C(=O)N(R$^A$)$_2$; —OC(=O)OR$^A$; —OC(=O)R$^A$; —OC(=O)N(R$^A$)$_2$; —NR$^A$C(=O)OR$^A$; or —C(R$^A$)$_3$; wherein each occurrence of R$^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^B$; —C(=O)R$^B$; —C(=O)N(R$^B$)$_2$; —CO$_2$R$^B$; —CN; —SCN; —SR$^B$; —SOR$^B$; —SO$_2$R$^B$; —NO$_2$; —N$_3$; —N(R$^B$)$_2$; —NHC(=O)R$^B$; —NR$^B$C(=O)N(R$^B$)$_2$; —OC(=O)OR$^B$; —OC(=O)R$^B$; —OC(=O)N(R$^B$)$_2$; —NR$^B$C(=O)OR$^B$; or —C(R$^B$)$_3$; wherein each occurrence of R$^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

or a pharmaceutically acceptable salt thereof, in an amount effective to treat the breast cancer or the ovarian cancer.

* * * * *